US012303235B2

(12) United States Patent
Addison et al.

(10) Patent No.: US 12,303,235 B2
(45) Date of Patent: May 20, 2025

(54) SYSTEMS AND METHODS FOR VIDEO-BASED MONITORING OF A PATIENT

(71) Applicant: Covidien LP, Mansfield, MA (US)

(72) Inventors: Paul S. Addison, Edinburgh (GB); Keith Batchelder, New York, NY (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/444,530

(22) Filed: Feb. 16, 2024

(65) Prior Publication Data

US 2024/0188831 A1 Jun. 13, 2024

Related U.S. Application Data

(63) Continuation of application No. 17/166,960, filed on Feb. 3, 2021, now Pat. No. 11,937,900, which is a
(Continued)

(51) Int. Cl.
A61B 5/1455 (2006.01)
A61B 5/00 (2006.01)
(Continued)

(52) U.S. Cl.
CPC .......... A61B 5/0077 (2013.01); A61B 5/1114 (2013.01); A61B 5/1117 (2013.01); A61B 5/1128 (2013.01); A61B 5/117 (2013.01); A61B 5/1455 (2013.01); A61B 5/14551 (2013.01); A61B 5/68 (2013.01); A61B 5/746 (2013.01); G16H 40/63 (2018.01); A61B 5/0006 (2013.01);
(Continued)

(58) Field of Classification Search
CPC ..... A61B 5/1455; A61B 5/0017; A61B 5/002; A61B 5/74; G16H 40/60; G16H 40/63
See application file for complete search history.

(56) References Cited

U.S. PATENT DOCUMENTS 5,107,845 A 4/1992 Guern et al.
5,408,998 A 4/1995 Mersch
(Continued)

FOREIGN PATENT DOCUMENTS

CA 2234191 A1 10/1998
CN 106725410 A 5/2017
(Continued)

OTHER PUBLICATIONS

Liu, Xinyl, et al., "An Image Captioning Method for Infant Sleeping Environment Diagnosis", Springer International Publishing, May 15, 2019, pp. 18-26, 9 pages.
(Continued)

Primary Examiner — Eric F Winakur
(74) Attorney, Agent, or Firm — Draft Masters IP, LLC

(57) ABSTRACT

The present invention relates to the field of medical monitoring, and in particular non-contact monitoring and communication with other medical monitoring devices. Systems and methods are described for receiving a video signal of a medical monitoring device that is outputting a light signal, identifying the light signal emitted by the medical monitoring device from the video signal, decoding information from the light signal, and determining a communication from the decoded information related to a patient being monitored or the medical monitoring device itself.

19 Claims, 10 Drawing Sheets

Related U.S. Application Data continuation of application No. 16/188,969, filed on Nov. 13, 2018, now Pat. No. 10,939,824.

(60) Provisional application No. 62/585,242, filed on Nov. 13, 2017.

(51) Int. Cl.
*A61B 5/11* (2006.01)
*A61B 5/117* (2016.01)
*G16H 10/60* (2018.01)
*G16H 40/63* (2018.01)

(52) U.S. Cl.
CPC .......... *A61B 5/0017* (2013.01); *A61B 5/0022* (2013.01); *A61B 2562/0219* (2013.01); *A61B 2562/08* (2013.01); *A61B 2576/00* (2013.01); *G06T 2207/10016* (2013.01); *G16H 10/60* (2018.01)

(56) References Cited

U.S. PATENT DOCUMENTS

| | | |
|---|---|---|
| 5,704,367 A | 1/1998 | Ishikawa et al. |
| 5,800,360 A | 9/1998 | Kisner et al. |
| 5,995,856 A | 11/1999 | Mannheimer et al. |
| 6,241,684 B1 | 6/2001 | Amano et al. |
| 6,668,071 B1 | 12/2003 | Minkin et al. |
| 6,920,236 B2 | 7/2005 | Prokoski |
| 7,431,700 B2 | 10/2008 | Aoki et al. |
| 7,558,618 B1 | 7/2009 | Williams |
| 8,149,273 B2 | 4/2012 | Liu et al. |
| 8,754,772 B2 | 6/2014 | Horng et al. |
| 8,792,969 B2 | 7/2014 | Bernal et al. |
| 8,971,985 B2 | 3/2015 | Bernal et al. |
| 9,226,691 B2 | 1/2016 | Bernal et al. |
| 9,282,725 B2 | 3/2016 | Jensen-Jarolim et al. |
| 9,301,710 B2 | 4/2016 | Mestha et al. |
| 9,402,601 B1 | 8/2016 | Berger et al. |
| 9,436,984 B2 | 9/2016 | Xu et al. |
| 9,443,289 B2 | 9/2016 | Xu et al. |
| 9,504,426 B2 | 11/2016 | Kyal et al. |
| 9,508,141 B2 | 11/2016 | Khachaturian et al. |
| 9,607,138 B1 | 3/2017 | Baldwin et al. |
| 9,662,022 B2 | 5/2017 | Kyal et al. |
| 9,693,693 B2 | 7/2017 | Farag et al. |
| 9,693,710 B2 | 7/2017 | Mestha et al. |
| 9,697,599 B2 | 7/2017 | Prasad et al. |
| 9,750,461 B1 | 9/2017 | Telfort |
| 9,839,756 B2 | 12/2017 | Klasek |
| 9,943,371 B2 | 4/2018 | Bresch et al. |
| 10,213,540 B2 | 2/2019 | Burbank et al. |
| 10,278,585 B2 | 5/2019 | Ferguson et al. |
| 10,376,147 B2 | 8/2019 | Wood et al. |
| 10,398,353 B2 | 9/2019 | Addison et al. |
| 10,447,972 B2 | 10/2019 | Patil |
| 10,489,912 B1 | 11/2019 | Brailovskiy |
| 10,523,852 B2 | 12/2019 | Tzvieli et al. |
| 10,588,779 B2 | 3/2020 | Vorhees et al. |
| 10,589,916 B2 | 3/2020 | Mcrae |
| 10,650,585 B2 | 5/2020 | Kiely |
| 10,667,723 B2 | 6/2020 | Jacquel et al. |
| 10,702,188 B2 | 7/2020 | Addison et al. |
| 10,729,357 B2 | 8/2020 | Larson et al. |
| 10,874,331 B2 | 12/2020 | Kaiser et al. |
| 10,937,296 B1 | 3/2021 | Kukreja et al. |
| 10,939,824 B2 | 3/2021 | Addison et al. |
| 10,939,834 B2 | 3/2021 | Khwaja et al. |
| 10,966,059 B1 | 3/2021 | Dayal et al. |
| 11,311,252 B2 | 4/2022 | Jacquel et al. |
| 11,315,275 B2 | 4/2022 | Addison et al. |
| 11,317,828 B2 | 5/2022 | Addison et al. |
| 11,350,850 B2 | 6/2022 | Jacquel et al. |
| 11,850,026 B2 | 12/2023 | Levi et al. |
| 2002/0137464 A1 | 9/2002 | Dolgonos et al. |
| 2004/0001633 A1 | 1/2004 | Caviedes |
| 2004/0258285 A1 | 12/2004 | Hansen et al. |
| 2005/0203348 A1 | 9/2005 | Shihadeh et al. |
| 2007/0116328 A1 | 5/2007 | Sablak et al. |
| 2008/0001735 A1 | 1/2008 | Tran |
| 2008/0108880 A1 | 5/2008 | Young et al. |
| 2008/0279420 A1 | 11/2008 | Masticola et al. |
| 2008/0295837 A1 | 12/2008 | Mccormick et al. |
| 2009/0024012 A1 | 1/2009 | Li et al. |
| 2009/0141124 A1 | 6/2009 | Liu et al. |
| 2009/0304280 A1 | 12/2009 | Aharoni et al. |
| 2010/0210924 A1 | 8/2010 | Parthasarathy et al. |
| 2010/0236553 A1 | 9/2010 | Jafari et al. |
| 2010/0249630 A1 | 9/2010 | Droitcour et al. |
| 2010/0324437 A1 | 12/2010 | Freeman et al. |
| 2011/0144517 A1 | 6/2011 | Cervantes |
| 2011/0150274 A1 | 6/2011 | Patwardhan et al. |
| 2012/0065533 A1 | 3/2012 | Carrillo et al. |
| 2012/0075464 A1 | 3/2012 | Derenne et al. |
| 2012/0195473 A1 | 8/2012 | De Haan et al. |
| 2012/0243797 A1 | 9/2012 | Di Venuto Dayer et al. |
| 2013/0073312 A1 | 3/2013 | Thompson et al. |
| 2013/0267873 A1 | 10/2013 | Fuchs |
| 2013/0271591 A1 | 10/2013 | Van Leest et al. |
| 2013/0272393 A1 | 10/2013 | Kirenko et al. |
| 2013/0275873 A1 | 10/2013 | Shaw et al. |
| 2013/0324830 A1 | 12/2013 | Bernal et al. |
| 2013/0324876 A1 | 12/2013 | Bernal et al. |
| 2014/0023235 A1 | 1/2014 | Cennini et al. |
| 2014/0052006 A1 | 2/2014 | Lee et al. |
| 2014/0053840 A1 | 2/2014 | Liu |
| 2014/0073860 A1 | 3/2014 | Urtti |
| 2014/0139405 A1 | 5/2014 | Ribble et al. |
| 2014/0140592 A1 | 5/2014 | Lasenby et al. |
| 2014/0235976 A1 | 8/2014 | Bresch et al. |
| 2014/0267718 A1 | 9/2014 | Govro et al. |
| 2014/0272860 A1 | 9/2014 | Peterson et al. |
| 2014/0275832 A1 | 9/2014 | Muehlsteff et al. |
| 2014/0276104 A1 | 9/2014 | Tao et al. |
| 2014/0330336 A1 | 11/2014 | Errico et al. |
| 2014/0334697 A1 | 11/2014 | Kersten et al. |
| 2014/0358017 A1 | 12/2014 | Op Den Buijs et al. |
| 2014/0378810 A1 | 12/2014 | Davis et al. |
| 2014/0379369 A1 | 12/2014 | Kokovidis et al. |
| 2015/0003723 A1 | 1/2015 | Huang et al. |
| 2015/0068069 A1 | 3/2015 | Tran et al. |
| 2015/0094597 A1 | 4/2015 | Mestha et al. |
| 2015/0131880 A1 | 5/2015 | Wang et al. |
| 2015/0157269 A1 | 6/2015 | Lisogurski et al. |
| 2015/0198707 A1 | 7/2015 | Al-Alusi |
| 2015/0223731 A1 | 8/2015 | Sahin |
| 2015/0238150 A1 | 8/2015 | Subramaniam |
| 2015/0265187 A1 | 9/2015 | Bernal et al. |
| 2015/0282724 A1 | 10/2015 | Mcduff et al. |
| 2015/0286779 A1 | 10/2015 | Bala et al. |
| 2015/0301590 A1 | 10/2015 | Furst et al. |
| 2015/0317814 A1 | 11/2015 | Johnston et al. |
| 2015/0379370 A1 | 12/2015 | Clifton et al. |
| 2016/0000335 A1 | 1/2016 | Khachaturian et al. |
| 2016/0049094 A1 | 2/2016 | Gupta et al. |
| 2016/0082222 A1 | 3/2016 | Garcia Molina et al. |
| 2016/0140828 A1 | 5/2016 | Deforest |
| 2016/0143598 A1 | 5/2016 | Rusin et al. |
| 2016/0151022 A1 | 6/2016 | Berlin et al. |
| 2016/0156835 A1 | 6/2016 | Ogasawara et al. |
| 2016/0174887 A1 | 6/2016 | Kirenko et al. |
| 2016/0210747 A1 | 7/2016 | Hay et al. |
| 2016/0235344 A1 | 8/2016 | Auerbach |
| 2016/0310084 A1 | 10/2016 | Banerjee et al. |
| 2016/0317041 A1 | 11/2016 | Porges et al. |
| 2016/0345931 A1 | 12/2016 | Xu et al. |
| 2016/0367186 A1 | 12/2016 | Freeman et al. |
| 2017/0007342 A1 | 1/2017 | Kasai et al. |
| 2017/0007795 A1 | 1/2017 | Pedro et al. |
| 2017/0055877 A1 | 3/2017 | Niemeyer |
| 2017/0065484 A1 | 3/2017 | Addison et al. |
| 2017/0071516 A1 | 3/2017 | Bhagat et al. |
| 2017/0095215 A1 | 4/2017 | Watson et al. |
| 2017/0095217 A1 | 4/2017 | Hubert et al. |

(56) References Cited

U.S. PATENT DOCUMENTS

| | | |
|---|---|---|
| 2017/0119340 A1 | 5/2017 | Nakai et al. |
| 2017/0147772 A1 | 5/2017 | Meehan et al. |
| 2017/0164904 A1 | 6/2017 | Kirenko |
| 2017/0172434 A1 | 6/2017 | Amelard et al. |
| 2017/0173262 A1 | 6/2017 | Veltz |
| 2017/0238805 A1 | 8/2017 | Addison et al. |
| 2017/0238842 A1 | 8/2017 | Jacquel et al. |
| 2017/0311887 A1 | 11/2017 | Leussler et al. |
| 2017/0319114 A1 | 11/2017 | Kaestle |
| 2018/0042486 A1 | 2/2018 | Yoshizawa et al. |
| 2018/0042500 A1 | 2/2018 | Liao et al. |
| 2018/0049669 A1 | 2/2018 | Vu et al. |
| 2018/0053392 A1 | 2/2018 | White et al. |
| 2018/0104426 A1 | 4/2018 | Oldfield et al. |
| 2018/0106897 A1 | 4/2018 | Shouldice et al. |
| 2018/0169361 A1 | 6/2018 | Dennis et al. |
| 2018/0217660 A1 | 8/2018 | Dayal et al. |
| 2018/0228381 A1 | 8/2018 | Leboeuf et al. |
| 2018/0303351 A1 | 10/2018 | Mestha et al. |
| 2018/0310844 A1 | 11/2018 | Tezuka et al. |
| 2018/0325420 A1 | 11/2018 | Gigi |
| 2018/0333050 A1 | 11/2018 | Greiner et al. |
| 2018/0333102 A1 | 11/2018 | De Haan et al. |
| 2018/0352150 A1 | 12/2018 | Purwar et al. |
| 2019/0050985 A1 | 2/2019 | Den Brinker et al. |
| 2019/0133499 A1 | 5/2019 | Auerbach |
| 2019/0142274 A1 | 5/2019 | Addison et al. |
| 2019/0199970 A1 | 6/2019 | Greiner et al. |
| 2019/0209046 A1 | 7/2019 | Addison et al. |
| 2019/0209083 A1 | 7/2019 | Wu et al. |
| 2019/0307365 A1 | 10/2019 | Addison et al. |
| 2019/0311101 A1 | 10/2019 | Nienhouse |
| 2019/0343480 A1 | 11/2019 | Shute et al. |
| 2019/0380599 A1 | 12/2019 | Addison et al. |
| 2019/0380807 A1 | 12/2019 | Addison et al. |
| 2020/0046302 A1 | 2/2020 | Jacquel et al. |
| 2020/0187827 A1 | 6/2020 | Addison et al. |
| 2020/0202154 A1 | 6/2020 | Wang et al. |
| 2020/0205734 A1 | 7/2020 | Mulligan et al. |
| 2020/0237225 A1 | 7/2020 | Addison et al. |
| 2020/0242790 A1 | 7/2020 | Addison et al. |
| 2020/0250406 A1 | 8/2020 | Wang et al. |
| 2020/0253560 A1 | 8/2020 | De Haan |
| 2020/0279464 A1 | 9/2020 | Llewelyn |
| 2020/0289024 A1 | 9/2020 | Addison et al. |
| 2020/0329976 A1 | 10/2020 | Chen et al. |
| 2020/0409383 A1 | 12/2020 | Maunder |
| 2021/0068670 A1 | 3/2021 | Redtel |
| 2021/0142874 A1 | 5/2021 | Llewelyn |
| 2021/0153746 A1 | 5/2021 | Addison et al. |
| 2021/0201517 A1 | 7/2021 | Yang et al. |
| 2021/0233631 A1 | 7/2021 | Llewelyn |
| 2021/0235992 A1 | 8/2021 | Addison |
| 2021/0295662 A1 | 9/2021 | Bugbee et al. |
| 2021/0313075 A1 | 10/2021 | Mc Namara et al. |
| 2022/0211296 A1 | 7/2022 | Addison et al. |
| 2023/0122367 A1 | 4/2023 | Tesar |

FOREIGN PATENT DOCUMENTS

| | | |
|---|---|---|
| CN | 111728602 A | 10/2020 |
| CN | 112233813 A | 1/2021 |
| DE | 19741982 A1 | 10/1998 |
| EP | 2793189 B1 | 11/2016 |
| EP | 2428162 B1 | 8/2017 |
| EP | 3207862 A1 | 8/2017 |
| EP | 3207863 A1 | 8/2017 |
| EP | 3384827 A1 | 10/2018 |
| EP | 2772828 B1 | 1/2019 |
| JP | 2004173010 A | 6/2004 |
| JP | 2004283373 A | 10/2004 |
| JP | 3744778 B2 | 12/2005 |
| JP | 2009544080 A | 12/2009 |
| JP | 2011130996 A | 7/2011 |
| KR | 101644843 B1 | 8/2016 |
| RS | 20120373 A1 | 4/2014 |
| WO | 2004100067 A2 | 11/2004 |
| WO | 2005079658 A2 | 9/2005 |
| WO | 2010034107 A1 | 4/2010 |
| WO | 2010036653 A1 | 4/2010 |
| WO | 2015059700 A1 | 4/2015 |
| WO | 2015078735 A1 | 6/2015 |
| WO | 2015110859 A1 | 7/2015 |
| WO | 2016065411 A1 | 5/2016 |
| WO | 2016178141 A1 | 11/2016 |
| WO | 2016209491 A1 | 12/2016 |
| WO | 2017060463 A1 | 4/2017 |
| WO | 2017089139 A1 | 6/2017 |
| WO | 2017100188 A2 | 6/2017 |
| WO | 2017144934 A1 | 8/2017 |
| WO | 2018042376 A1 | 3/2018 |
| WO | 2019094893 A1 | 5/2019 |
| WO | 2019135877 A1 | 7/2019 |
| WO | 2019240991 A1 | 12/2019 |
| WO | 2020033613 A1 | 2/2020 |
| WO | 2021044240 A1 | 3/2021 |

OTHER PUBLICATIONS

Zaunseder, et al., "Spatio-temporal analysis of blood perfusion by imaging photoplethysmography," Progress in Biomedical Optics and Imaging, SPIE—International Society for Optical Engineering, vol. 10501, Feb. 20, 2018, 15 pages.

Zhou, J., et al., "Maximum parsimony analysis of gene copy number changes in tumor phylogenetics," 15th International Workshop on Algorithms in Bioinformatics WABI 2015, Atlanta, USA, 2015, pp. 108-120, 13 pages.

Kwon, Sungjun, et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177, 4 pages.

Lai, C.J., et al., "Heated humidified high-flow nasal oxygen prevents intraoperative body temperature decrease in non-intubated thoracoscopy", Journal of Anesthesia, Oct. 15, 2018, 8 pages.

Lawrence, E., et al., "Data Collection, Correlation and Dissemination of Medical Sensor information in a WSN", IEEE 2009 Fifth International Conference on Networking and Services, 978-0-7695-3586-9/09, Apr. 20, 2009, pp. 402-408, 7 pages.

Li, et al., "A Non-Contact Vision-Based System for Respiratory Rate Estimation", IEEE 978-1-4244-7929-0/14, 2014, pp. 2119-2122, 4 pages.

Liu, H., et al., "A Novel Method Based on Two Cameras for Accurate Estimation of Arterial Oxygen Saturation", BioMedical Engineering Online, vol. 14, No. 52, 2015, 18 pages.

Liu, S., et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

Liu, C., et al., "Motion Magnification", ACM Transactions on Graphics (TOG), vol. 24, No. 3, 2005, pp. 519-526, 8 pages.

Lv, et al., "Class Energy Image Analysis for Video Sensor-Based Gait Recognition: a Review", Sensors, No. 15, 2015, pp. 932-964, 33 pages.

Mcduff, Daniel J., et al., "A Survey of Remote Optical Photoplethysmographic Imaging Methods", IEEE 987-1-4244-0270-1/15, 2015, pp. 6398-6404, 7 pages.

Mestha, L.K., et al., "Towards Continuous Monitoring of Pulse Rate in Neonatal Intensive Care Unit with a Webcam", Proc. of 36th Annual Int. Conf. of the IEEE Engineering in Medicine and Biology Society, Chicago, IL, 2014, pp. 3817-3820, 4 pages.

Mukherjee, S., et al., "Patient health management system using e-health monitoring architecture", IEEE, International Advance Computing Conference (IACC), 978-1-4799-2572-8/14, Feb. 21, 2014, pp. 400-405, 6 pages.

Nguyen, et al., "3D shape, deformation and vibration measurements using infrared Kinect sensors and digital image correlation", Applied Optics, vol. 56, No. 32, Nov. 10, 2017, 8 pages.

(56) References Cited

OTHER PUBLICATIONS

Ni, et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.

Nisar, et al., "Contactless heart rate monitor for multiple persons in a video", IEEE International Conference on Consumer Electronics—Taiwan (ICCE-TW), XP03291229 [Retreived on Jul. 25, 2016], May 27, 2016, 2 pages.

Pereira, C., et al., "Noncontact Monitoring of Respiratory Rate in Newborn Infants Using Thermal Imaging", IEEE Transactions on Biomedical Engineering, Aug. 23, 2018, 10 pages.

Poh, et al., "Advancements in Noncontact, Multiparameter Physiological Measurements Using a Webcam", IEEE Transactions on Biomedical Engineering, vol. 58, No. 1, Jan. 2011, pp. 7-11, 5 pages.

Poh, et al., "Non-contact, automated cardiac pulse measurements using video imaging and blind source separation", OPT. Express 18, 2010, p. 10762-10774, 14 pages.

Povsic, Klemen, et al., "Real-Time 3D visualization of the thoracoabdominal surface during breathing with body movement and deformation extraction", Physiological Measurement, vol. 36, No. 7, May 28, 2015, pp. 1497-1516, 22 pages.

Prochazka, et al., "Microsoft Kinect Visual and Depth Sensors for Breathing and Heart Rate Analysis", Senors, vol. 16, No. 7, Jun. 28, 2016, 11 pages.

Rajan, V., et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.

Rajan, V., et al., "Dependency Clustering of Mixed Data with Gaussian Mixture Copulas", 25th International Joint Conference on Artificial Intelligence IJCAI, New York, USA, 2016, pp. 1967-1973, 7 pages.

Reisner, A., et al., "Utility of the Photoplethysmogram in Circulatory Monitoring", American Society of Anesthesiologist, May 2008, pp. 950-958, 9 pages.

Reyes, B.A., et al., "Tidal Volume and Instantaneous Respiration Rate Estimation using a Volumetric Surrogate Signal Acquired via a Smartphone Camera", IEEE Journal of Biomedical and Health Informatics, vol. 21(3), Feb. 25, 2016, pp. 764-777, 15 pages.

Rezaei, Mahdi, et al., "DeepSOCIAL: Social Distancing Monitoring and Infection Risk Assessment in COVID-19 Pandemic", Applied Sciences, vol. 10, 7514, Oct. 26, 2020, pp. 1-29, 29 pages.

Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622, 12 pages.

Rubinstein, M, "Analysis and Visualization of Temporal Variations in Video", Department of Electrical Engineering and Computer Science, Massachusetts Institute of Technology, Feb. 2014, 118 pages.

Sathyamoorthy, Adarsh Jagan, et al., "COVID-Robot: Monitoring Social Distancing Constraints in Crowded Scenarios", Aug. 21, 2020, pp. 1-11, 11 pages.

Scalise, Lorenzo, et al., "Heart rate measurement in neonatal patients using a webcamera", Department of Industrial Engineering and Mathematical Science, Italy, 978-1-4673-0882-3/12, EEE, 2012, 4 pages.

Schaerer, J., et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.

Sengupta, A., et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.

Shah, Nitin, et al., "Performance of three new-generation pulse oximeters during motion and low perfursion in volunteers", Journal of Clinical Anesthesia, No. 24, 2012, pp. 385-391, 7 pages.

Shao, Dangdang, et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.

Shrivastava, H., et al., "Classification with Imbalance: A Similarity-based Method for Predicting Respiratory Failure", IEEE International Conference on Bioinformatics and Biomedicine (IEEE BIBM2015), Washington, DC, USA, 2015, pp. 707-714, 8 pages.

Sokooti, Hess, et al., "Hierarchical Prediction of Registration Misalignment Using a Convolutional LSTM: Application to Chest CT Scans", IEEE Access, IEEE, USA, vol. 9, Apr. 20, 2021, 62008-62020, 13 pages.

Srinivas, J., et al., "A Mutual Authentication Framework for Wireless Medical Sensor Networks", Journal of Medical Systems, 41:80, 2017, pp. 1-19, 19 pages.

Sun, Yu, et al., "Motion-compensated noncontact imaging photoplethysmography to monitor cardiorespiratory status during exercise", Journal of Biomedical Optics, vol. 16, No. 7, Jul. 1, 2011, 10 pages.

Sun, Yu, et al., "Noncontact imaging photoplethysmography to effectively access pulse rate variability", Journal of Biomedical Optics, vol. 18(6), Jun. 2013, 10 pages.

Tamura, et al., "Wearable Photoplethysmographic Sensors-Past & Present", Electronics, vol. 3, 2014, pp. 282-302, 21 pages.

Tarassenko, L., et al., "Non-contact video-based vital sign monitoring using ambient light and auto-regressive models", Institute of Physics and Engineering in Medicine, vol. 35, 2014, pp. 807-831, 26 pages.

Teichmann, D., et al., "Non-Contact monitoring techniques-Principles and applications", In Proc. of IEEE International Conference of the Engineering in Medicine and Biology Society (EMBC), San Diego, CA, 2012, pp. 1302-1305, 4 pages.

Transue, S., et al., "Real-time Tidal Volume Estimation using Iso-surface Reconstruction", 2016 IEEE First International Conference on Connected Health: Applications, Systems and Engineering Technologies (CHASE), Jun. 27, 2016, pp. 209-218, 10 pages.

Verkruysee, Wim, et al., "Calibration of Contactless Pulse Oximetry", Anesthesia & Analgesia, vol. 124, No. 1, Jan. 2017, pp. 136-145, 10 pages.

Villarroel, Mauricio, et al., "Continuous non-contact vital sign monitoring in neonatal intensive care unit", Healthcare Technology Letters, vol. 1, Issue 3, 2014, pp. 87-91, 5 pages.

Wadhwa, N., et al., "Phase-Based Video Motion Processing", MIT Computer Science and Artificial Intelligence Lab, Jul. 2013, 9 pages.

Wadhwa, N., et al., "Riesz pyramids for fast phase-based video magnification", In Proc. of IEEE International Conference on Computational Photography (ICCP), Santa Clara, CA, 2014, 10 pages.

Wang, W., et al., "Exploiting spatial redundancy of image sensor for motion robust rPPG", IEEE Transactions on Biomedical Engineering, vol. 62, No. 2, 2015, pp. 415-425, 11 pages.

Wu, H.Y., et al., "Eulerian video magnifcation for revealing subtle changes in the world", ACM Transactions on Graphics (TOG), vol. 31, No. 4, 2012, pp. 651-658, 8 pages.

Wulbrand, H., et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.

Yu, M.C., et al., "Noncontact Respiratory Measurement of vol. Change Using Depth Camera", 2012 Annual International Conference of the IEEE Engeineering in Medicine and Biology Society, Aug. 28, 2012, pp. 2371-2374, 4 pages.

"European Search Report", European Application No. 17156334.9, Applicant: Covidien LP, Aug. 23, 2017, 10 pages.

"European Search Report", European Patent Application No. 17156337.2, Applicant: Covidien LP, Aug. 23, 2017, 10 pages.

"International Search Report and Written Opinion", International Application No. PCT/US2021/015669, Apr. 12, 2021, 15 pages.

(56) References Cited

OTHER PUBLICATIONS

"International Search Report and Written Opinion", International Application No. PCT/US2018/060648, Jan. 28, 2019, 17 pages.
"International Search Report and Written Opinion", International Application No. PCT/US2018/065492, Mar. 8, 2019, 12 pages.
"International Search Report and Written Opinion", International Application No. PCT/US2019/035433, Nov. 11, 2019, 17 pages.
"International Search Report and Written Opinion", International Application No. PCT/US2019/045600, Oct. 23, 2019, 19 pages.
"Invitation to Pay Additional Fees and Partial International Search Report", International Application No. PCT/US2019/035433, Sep. 13, 2019, 16 pages.
"Medical Electrical Equipment, Part 2-61: Particular requirements for basic safety and essential performance of pulse oximeter equipment", BSI Standards Publication, BS EN ISO 80601-2-61, 2011, 98 pages.
Aarts, Lonneke A.M., et al., "Non-contact heart rate monitoring utilizing camera photoplethysmography in neonatal intensive care unit—A Pilot Study", Early Human Development 89, 2013, pp. 943-948, 6 pages.
Abbas, A.K., et al., "Neonatal non-contact respiratory monitoring based on real-time infrared thermography", Biomed. Eng. Online, vol. 10, No. 93, 2011, 17 pages.
Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.
Addison, Paul S., et al., "Developing an algorithm for pulse oximetry derived respirator rate (RRoxi): a healthy volunteer study", J Clin comput, No. 26, 2012, pp. 45-51, 7 pages.
Addison, Paul S., et al., "Pulse oximetry-derived respiratory rate in general care floor patients", J. Clin Monit Comput, No. 29, 2015, pp. 113-120, 8 pages.
Addison, P.S., et al., "Video-based Heart Rate Monitoring across a Range of Skin Pigmentations during an Acute Hypoxic Challenge", J Clin Monit Comput, vol. 9, Nov. 9, 2017, 15 pages.
Al-Naji, Ali, et al., "Real Time Apnoea Monitoring of Children Using the Microsoft Kinect Sensor: a Pilot Study", Sensors, 17(286), Feb. 3, 2017, 15 pages.
Amazon, "Dockem Koala Tablet Wall Mount Dock for ipad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.
Amelard, et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.
Armanian, A. M., "Caffeine administration to prevent apnea in very premature infants", Pediatrics & Neonatology, 57 (5), 2016, pp. 408-412, 5 pages.
Barone, S, et al., "Computer-aided modelling of three-dimensional maxillofacial tissues through multi-modal imaging", Proceedings of the Institution of Mechanical Engineers, Journal of Engineering in Medicine, Part H vol. 227, No. 2, Feb. 1, 2013, 1 page.
Barone, S, et al., "Creation of 3D Multi-body Orthodontic Models by Using Independent Imaging Sensors", Senros Mdpi Ag Switzerland, vol. 13, No. 2, Jan. 1, 2013, pp. 2033-2050, 18 pages.
Bartula, M., et al., "Camera-based System for Sontactless Monitoring of Respiration", 2013 35th Annual International Conference of the IEEE Engineering in Medicine and Biology Society (EMBC), Jul. 3, 2013, pp. 2672-2675, 4 pages.
Bhattacharya, S., et al., "A Novel Classification Method for Predicting Acute Hypotensive Episodes in Critical Care", 5th ACM Conference on Bioinformatics, Computational Bilogy and Health Informatics (ACM-BCB 2014), Newport Beach, USA, 2014, 10 pages.
Bhattacharya, S., et al., "Unsupervised learning using Gaussian Mixture Copula models", 21st International Conference on Computational Statistics (COMPSTAT 2014), Geneva, Switzerland, 2014, pp. 523-530, 8 pages.
Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.
Bousefsaf, Frederic, et al., "Continuous wavelet filtering on webcam photoplethysmographic signals to remotely assess the instantaneous heart rate", Biomedical Signal Processing and Control 8, 2013, pp. 568-574, 7 pages.
Bruser, C., et al., "Adaptive Beat-to-Beat Heart Rate Estimation in Ballistocardiograms", IEEE Transactions Information Technology in Biomedicine, vol. 15, No. 5, Sep. 2011, pp. 778-786, 9 pages.
Cennini, Giovanni, et al., "Heart rate monitoring via remote photoplethysmography with motion artifacts reduction", Optics Express, vol. 18, No. 5, Mar. 1, 2010, pp. 4867-4875, 9 pages.
Colantonio, S., et al., "A smart mirror to promote a healthy lifestyle", Biosystems Engineering. vol. 138, Innovations in Medicine and Healthcare, Oct. 2015, pp. 33-43, 11 pages.
Cooley, et al., "An Alorithm for the Machine Calculation of Complex Fourier Series", Aug. 17, 1964, pp. 297-301, 5 pages.
Di Fiore, J.M., et al., "Intermittent hypoxemia and oxidative stress in preterm infants", Respiratory Physiology & Neurobiology, No. 266, 2019, pp. 121-129, 25 pages.
Fei, J., et al., "Thermistor at a distance: unobtrusive measurement of breathing", IEEE Transactions on Biomedical Engineering, vol. 57, No. 4, 2010, pp. 968-998, 11 pages.
Feng, Litong, et al., "Dynamic ROI based on K-means for remote photoplethysmography", IEE International Conference on Accoustics, Speech and Signal Processing (ICASSP), Apr. 2015, pp. 1310-1314, 5 pages.
Fischer, et al., "ReMoteCare: Health Monitoring with Streaming Video", OCMB '08, 7TH International Conference on Mobile Business, IEEE, Piscataway, NJ,, Jul. 7, 2008, pp. 280-286.
George, et al., "Respiratory Rate Measurement From PPG Signal Using Smart Fusion Technique", International Conference on Engineering Trends and Science & Humanities (ICETSH-2015), 2015, 5 pages.
Goldman, L.J., "Nasal airflow and thoracoabdominal motion in children using infrared thermographic video processing", Pediatric Pulmonology, vol. 47, No. 5, 2012, pp. 476-486, 11 pages.
Grimm, T., et al., "Sleep position classification from a depth camera using bed aligned maps", 23rd International Conference on Pattern Recognition (ICPR), Dec. 2016, pp. 319-324, 6 pages.
Gsmarena, "Apple iPad Pro 11 (2018)", https://www.gsmarena.com/apple_ipad_pro_11_(2018)-9386.pjp, viewed on Nov. 16, 2021, 1 page.
Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.
Han, J., et al., "Visible and infrared image registration in man-made environments employing hybrid visuals features", Pattern Recognition Letters, vol. 34, No. 1, 2013, pp. 42-51, 10 pages.
Harte, James M., et al., "Chest wall motion analysis in healthy volunteers and adults with cystic fibrosis using a novel Kinect-based motion tracking system", Medical & Biological Engineering & Computing, 54(11), Feb. 13, 2016, pp. 1631-1640, 11 pages.
Huddar, V., et al., "Predicting Postoperative Acute Respiratory Failure in Critical Care using Nursing Notes and Physiological Signals", 36th Annual International Conference of IEEE Engineering in Medicine and Biology Society (IEEE Embc 2014), Chicago, USA, 2014, pp. 2702-2705, 4 pages.
Hyvarinen, A., et al., "Independent Component Analysis: Algorithms and Applications", Neural Networks, vol. 13, No. 4, 2000, pp. 411-430, 31 pages.
Javadi, M., et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.

(56) References Cited

OTHER PUBLICATIONS

Jopling, M. W., et al., "Issues in the Laboratory Evaluation of Pulse Oximeter Performance", Anesth. Analg., No. 94, 2002, pp. S62-S68, 7 pages.

Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.

Klaessens, J.H.G.M., et al., "Non-invasive skin oxygenation imaging using a multi-spectral camera system: Effectiveness of various concentration algorithms applied on human skin", Proc. of SPIE, vol. 7174 717408-1, 2009, 14 pages.

Kong, Lingqin, et al., "Non-contact detection of oxygen saturation based on visible light imaging device using ambient light", Optics Express, vol. 21, No. 15, Jul. 29, 2013, pp. 17646-17471, 8 pages.

Kortelainen, J.M., et al., "Sleep staging based on signals acquired through bed sensor", IEEE Transactions on Informational Technology in Biomedicine, vol. 14, No. 3, May 2010, pp. 776-785, 10 pages.

Kumar, M., et al., "Distance PPG: Robust non-contact vital signs monitoring using a camera",Express, vol. 6, No. 5, May 1, 2015, 24 pages.

SYSTEMS AND METHODS FOR VIDEO-BASED MONITORING OF A PATIENT

CROSS-REFERENCE TO RELATED APPLICATION(S)

The present application is a continuation application of U.S. application Ser. No. 17/166,960 filed Feb. 3, 2021, which is a continuation application of U.S. application Ser. No. 16/188,969 filed Nov. 13, 2018, entitled "SYSTEMS AND METHODS FOR VIDEO-BASED MONITORING OF A PATIENT", now U.S. Pat. No. 10,939,824 issued Mar. 9, 2021, which claims the benefit of priority to U.S. Provisional Patent Application No. 62/585,242, filed Nov. 13, 2017, the disclosure of which is incorporated herein by reference in its entirety.

BACKGROUND

Many conventional medical monitors require attachment of a sensor to a patient in order to detect physiological signals from the patient and transmit detected signals through a cable to the monitor. These monitors process the received signals and determine vital signs such as the patient's pulse rate, respiration rate, and arterial oxygen saturation. For example, a pulse oximeter is a finger sensor that may include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, and others. Some wireless, wearable sensors have been developed, such as wireless EEG patches and wireless pulse oximetry sensors.

Video-based monitoring is a new field of patient monitoring that uses a remote video camera to detect physical attributes of the patient. This type of monitoring may also be called "non-contact" monitoring in reference to the remote video sensor, which does not contact the patient. The remainder of this disclosure offers solutions and improvements in this new field.

SUMMARY

In an embodiment described herein, a video-based method of monitoring a patient includes receiving, from a video camera, a video signal having a field of view exposed to light emitted by a pulse oximeter; identifying, using a processor, the light emitted by the pulse oximeter in the video signal; decoding, using the processor, the encoded information of the light emitted by the pulse oximeter; and determining, using the processor, from the decoded information a communication, the communication being at least one of a first communication related to a patient associated with the pulse oximeter, and a second communication related to the pulse oximeter.

In some embodiments, the encoded information is encoded using frequency modulation.

In some embodiments, the encoded information is encoded using pulse width modulation.

In some embodiments, the communication includes the first communication, the first communication is determined from the decoded information, and the first communication includes a unique identifier associated with the patient.

In some embodiments, the communication includes the first communication, the first communication is determined from the decoded information, and the first communication includes a vital sign measurement of the patient.

In some embodiments, the communication includes the second communication, the second communication is determined from the decoded information, and the second communication includes an alert condition of the pulse oximeter.

In some embodiments, the communication includes the second communication, the second communication is determined from the decoded information, and the second communication includes equipment identifying information of the pulse oximeter.

In some embodiments, the video-based method of monitoring a patient further includes determining, using the processor, a unique identifier associated with the patient from the video signal and associating, using the processor, the unique identifier associated with the patient with the equipment identifying information of the pulse oximeter.

In some embodiments, the light emitted by the pulse oximeter is used by the pulse oximeter to measure a vital sign of the patient.

In some embodiments, the light emitted by the pulse oximeter is a dedicated light for the purpose of sending the encoded information.

In some embodiments, the dedicated light is at an outer portion of a probe of the pulse oximeter, at a cable of the pulse oximeter, or at a base of the pulse oximeter.

In some embodiments, the video-based method of monitoring a patient further includes identifying from the video signal at a first time, using the processor, a first position within the field of view of the video camera at which the light is emitted by the pulse oximeter.

In some embodiments, the video-based method of monitoring a patient further includes identifying from the video signal at a second time, using the processor, a second position at which the light is emitted by the pulse oximeter.

In some embodiments, the video-based method of monitoring a patient further includes determining, using the processor, that the first position is different from the second position by a threshold amount.

In some embodiments, the video-based method of monitoring a patient further includes determining based on the threshold amount, using the processor, that the pulse oximeter has moved beyond the field of view of the video camera or has moved a predetermined distance within the field of view of the video camera.

In some embodiments, the video-based method of monitoring a patient further includes associating, using the processor, at least one of the first position and the second position with at least one of a bed identifier, a room identifier, a floor identifier, and a facility identifier.

In some embodiments, the video-based method of monitoring a patient further includes sending, using the processor, a video camera control signal instructing the camera to change its field of view.

In some embodiments, the video camera control signal instructs the camera to at least one of: focus the field of view at the first position; zoom in the field of view at the first position; and center the field of view at the first position.

In another embodiment described herein, a method of communicating information from a patient monitoring device includes determining, using a processor, information related to at least one of a pulse oximeter and a patient associated with the pulse oximeter; encoding the information according to a transmission scheme; and emitting, from the pulse oximeter, a light signal with the encoded information according to the transmission scheme. The light signal is emitted in a field of view captured by a video camera.

In another embodiment described herein, a system for video-based monitoring of a patient includes a video camera configured to capture a video signal having a field of view, a pulse oximeter, and a video processing device in communication with the camera. The pulse oximeter is configured to determine information related to at least one of the pulse oximeter and a patient associated with the pulse oximeter; encode the information according to a transmission scheme; and emit, from the pulse oximeter, a light signal with the encoded information according to the transmission scheme. The light signal is emitted within the field of view of the video camera. The video processing device in communication with the camera is configured to receive, from the video camera, the video signal including the light signal as captured by the video camera; identify the light signal emitted by the pulse oximeter in the video signal; and decode the encoded information of the light signal emitted by the pulse oximeter. Decoding the encoded information yields decoded information.

In another embodiment described herein, a pulse oximeter comprises a processing resource configured to determine information related to at least one of the pulse oximeter and a patient associated with the pulse oximeter and to encode the information according to a transmission scheme. The pulse oximeter can further comprise an emitter configured to emit, from the pulse oximeter, a light signal with the encoded information according to the transmission scheme.

In another embodiment described herein, a video processing device in communication with a video camera is configured to receive, from the video camera, a video signal; identify in the video signal a light signal emitted by a pulse oximeter; and decode encoded information of the light signal emitted by the pulse oximeter to yield decoded information.

Features in one aspect or embodiment may be applied as features in any other aspect or embodiment, in any appropriate combination. For example, any one of system, method, pulse oximeter, or device features may be applied as any one or more other of system, method, pulse oximeter, or device features.

DETAILED DESCRIPTION

The present invention relates to the field of medical monitoring, and in particular non-contact monitoring and communication with other medical monitoring devices. Systems and methods are described for receiving a video signal of a medical monitoring device that is outputting a light signal, identifying the light signal emitted by the medical monitoring device from the video signal, decoding information from the light signal, and determining a communication from the decoded information related to a patient being monitored or the medical monitoring device itself. The video signal is detected by a camera that views but does not contact the patient. With appropriate selection and filtering of the video signal detected by the camera, a light signal can be detected and decoded from the video signal. For example, a patient may wear a pulse oximeter to measure the patient's pulse or other information. The pulse oximeter may include a light that transmits information via a transmission scheme (e.g., pulse width modulation, frequency modulation, etc.). This information can be decoded from the video signal captured by the video camera. The information may include information about the pulse oximeter, such as a unique identification number of the pulse oximeter device. The information may also include other types of information, such as information about the patient (e.g., the pulse rate as measured by the pulse oximeter device). This approach has the potential to improve recordkeeping, improve patient care, reduce errors in vital sign measurements, increase confidence in measurements taken, help healthcare providers better characterize and respond to alarm conditions of a medical monitoring device, and improve tracking of patient identification and location, along with many other potential advantages discussed below.

Figure 1A:
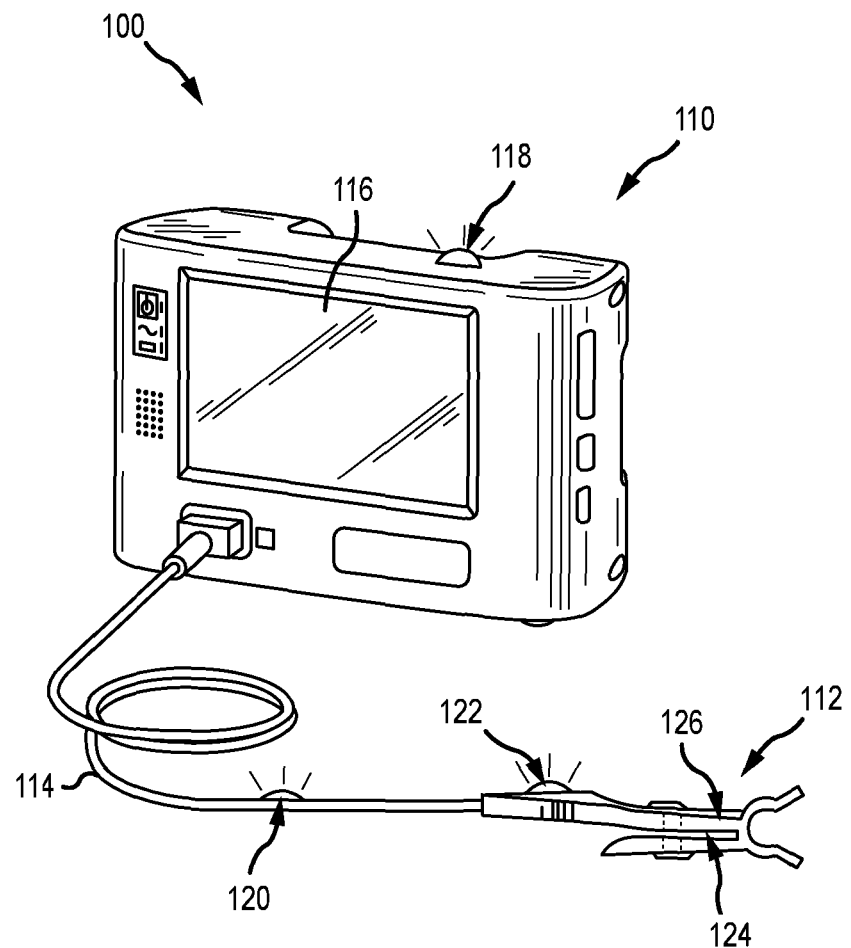
FIG. 1A is a perspective view of a pulse oximetry monitor and sensor according to various embodiments described herein.

FIG. 1A is a perspective view of a pulse oximetry monitor and sensor according to an embodiment of the invention. A monitoring system 100 is shown in FIG. 1A. The system 100 includes a monitor 110 and a sensor 112 connected to the monitor 110 by a cable 114. In the example of FIG. 1, the monitor 110 is a pulse oximeter, and the sensor 112 is a finger sensor including two light emitters and a photodetector. Other types of monitors and sensors may be used. The sensor 112 emits light into the patient's finger, detects light transmitted through the patient's finger, and transmits the detected light signal through the cable 114 to the monitor 110. The monitor 110 includes a processor that processes the signal, determines vital signs (including e.g., pulse rate, respiration rate, and arterial oxygen saturation, etc.), and displays them on an integrated display 116. In some embodiments, the sensor 112 may not have a photodetector. In such embodiments, the vital sign measurement may be determined solely based on the light from the sensor 112 captured by the video camera of a system. In other words, the sensor 112 itself would just be a light emitter and would not have a sensor such as a photodetector or other optical detector.

The light emitted from the sensor 112 to measure a vital sign of the patient at an opening 124 may also be used to encode information that can be read by a video camera or other optical sensing device that can pick up the light emitted from the sensor 112. Some of that light escapes or leaks through the opening 124 and therefore can be sensed by a video camera or other optical sensing device. In some embodiments, the sensor 112 has a translucent, transparent, or cut out portion that lets the light emitted from the sensor 112 escape the sensor 112 at other locations than just through the opening 124. For example, a translucent, transparent, or cut out portion of the sensor 112 may exist at the top of the sensor 112 at a location 126. In some embodiments, the translucent, transparent, or cut out portion may exist elsewhere on the sensor 112, such as on one of the sides or the bottom of the sensor 112.

In some embodiments, the monitoring system 100 has a light other than the light emitted by the sensor 112 to measure a vital sign of a patient. For example, a light could be placed at different locations on the monitor 110, cable 114, or sensor 112, as shown by lights 118, 120, and 122. Various embodiments of the monitoring system 100 may have none, one, two, or all of the lights shown in FIG. 1A. Any one of the lights that are present can be used to encode information to be sensed by a video camera or other optical capture device. Different light locations may have different advantages. For example, the light 122 may be advantageous for systems that correlate the sensor 112 with a patient for more advanced patient video monitoring. Examples of such techniques are described in U.S. patent application Ser. No. 15/432,063, titled "Systems and Methods for Video-Based Monitoring of Vital Signs" and U.S. patent application Ser. No. 15/432,057 with the same title, the disclosures of each of which are incorporated herein in their entirety. The sensor 112 is worn by the patient being monitored, and a video-based monitoring system (not shown) may monitor the patient using methods that analyze the video of a patient's face. Accordingly, it may be important to accurately identify the patient that is wearing the sensor 112. Since the light 122 may be closer to the patient than, for example, the light 118 would be, the system may have a higher confidence level that the measurements associated with a patient's face are for the same patient with which communications from the light 122 are associated. That the light 122 is closer to the patient than the light 118 may also be advantageous where a single camera is monitoring multiple patients, so that the system can accurately associate a contact sensor with the correct patient in the field of view of the video camera. It may be more difficult, in some scenarios with multiple patients, for a non-contact monitoring system to have confidence that a light farther away from a patient, such as the light 118, is associated with a particular patient (especially if there are multiple patients in the field of view of the camera). If the light 118 is used, it advantageously may be able to continue to transmit signals if the patient's hand is out of view of the video camera (e.g., if the patient's hand is under a blanket). The light 120 may offer a balance of these two advantages. Lights may also be located at other locations of the monitoring system 100. In some embodiments, multiple lights at multiple locations on the same monitoring system 100 may be used. This may offer redundancies and advantages of various individual lights. The multiple lights may be utilized to send the same, synchronized signal, increasing the chance that the signal will be picked up or visible to the camera. In some embodiments, the multiple lights may transmit different signals, effectively increasing the bandwidth of the monitoring system 100 for transmitting messages.

In some embodiments, the monitoring system may also have an optical sensor to receive optical signals as well. For example, an optical sensor may be a visible light sensor or an infrared sensor. Such an optical sensor could be located at any of the locations where lights are shown (e.g., at lights 118, 120, 122) or at other locations of the monitoring system 100. The lights 118, 120, and 122 may be a light emitting diode (LED) or any other type of light. The lights could also be another type of emitter, such as an infrared light. Other types of sensors and emitters may also be used, such as radio frequency (RF) transmitters and receivers, including radio-frequency identification (RFID) devices. Regardless of the type of emitters and receivers used, various embodiments include systems capable of one or two-way communication between the non-contact monitoring system and a contact monitoring sensor. In such embodiments, the optical sensor allows the monitoring system 100 to receive signals in addition to emitting signals using the lights of the monitoring system 100. For example, an optical sensor may receive a message indicating a request for information. The request for information may be a request for vital sign information measured by the monitoring system 100. In response, whichever light(s) 118, 120, or 122 is present at the monitoring system 100 transmits the requested information. Another request for information may include a request for equipment identifying information of the monitoring system 100. Such information may include a unique identifier of the monitoring system 100, information about how the monitoring system 100 functions (e.g., capabilities, equipment specifications, etc.), information about the manufacturer or model number of the monitoring system 100, default or custom settings of the monitoring system 100, information input into the monitor 110 about the patient being monitored, a calibration sequence for the monitoring system 100 to ensure that the video camera has accurately located a light source of the monitoring system 100, or any other information related to the monitoring system 100.

Figure 1B:
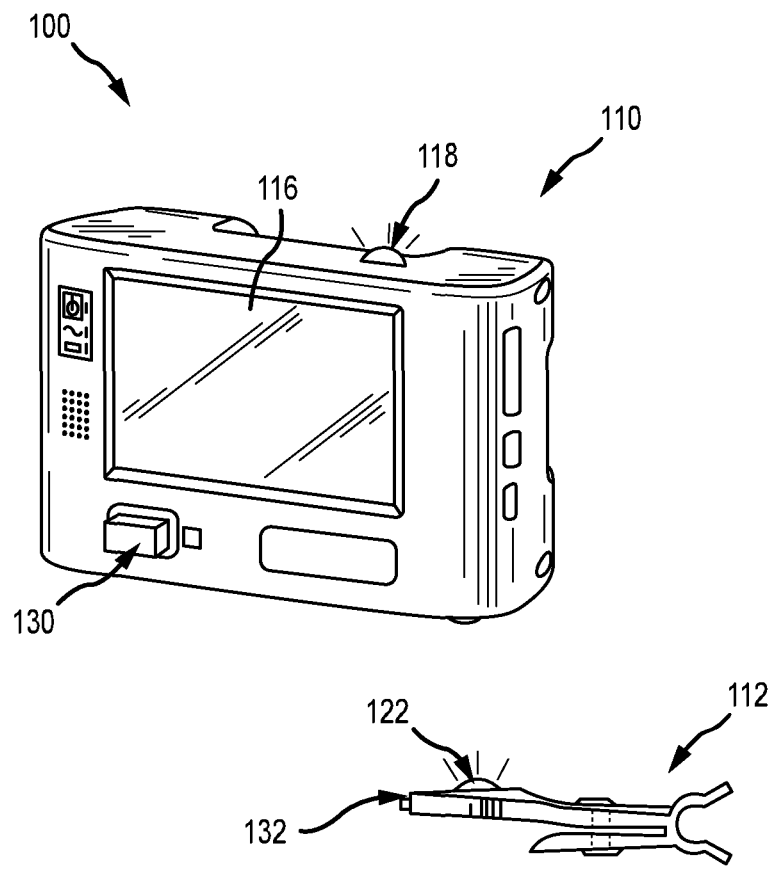
FIG. 1B is a perspective view of a wireless pulse oximetry monitor and sensor according to various embodiments described herein.

FIG. 1B is a perspective view of a wireless pulse oximetry monitor and sensor according to an embodiment of the invention. The monitor and sensor of FIG. 1B are similar to those of FIG. 1A, except that the sensor 112 communicates with the monitor 110 wirelessly. Accordingly, the monitor 110 has a receiver 130 that receives wireless signals from a transmitter 132 of the sensor 112. In some embodiments, the signals transmitted by the transmitter 132 of the sensor 112 may be captured by a video camera or other optical capture device as disclosed herein. Since the wireless monitor 110 and sensor 112 does not have a cord, there is no option for a light on the cord. However, one, both, or none of the lights 118 and 122 may exist and function as disclosed herein. In some embodiments, signals can be sent from the monitor 110 to the sensor 112. For example, if a signal from the monitor requests a certain type of data, the lights 118 and/or 122 can be used to send a response message including the data requested. A processor at the monitor 110 is used to determine what data is requested and to send the responsive signal.

Figure 2A:
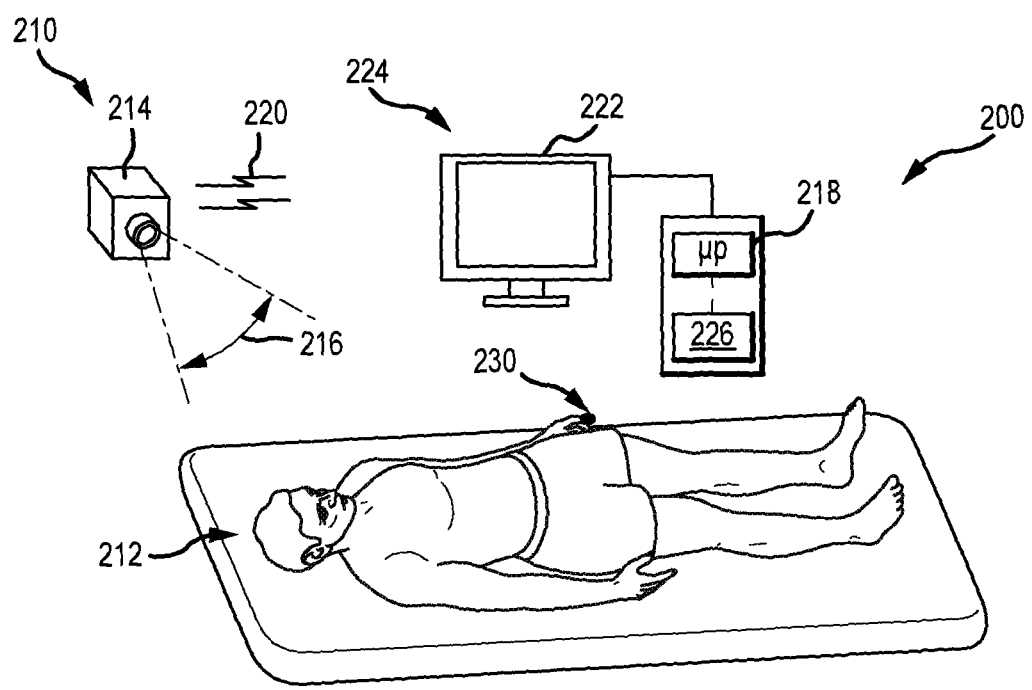
FIG. 2A is a schematic view of a video-based patient monitoring system according to various embodiments described herein.

FIG. 2A is a schematic view of a video-based patient monitoring system 200 and a patient 212 according to an embodiment of the invention. The system 200 includes a non-contact detector 210 placed remote from the patient 212. In this embodiment, the detector 210 includes a camera 214, such as a video camera. The camera 214 is remote from the patient, in that it is spaced apart from and does not contact the patient 212. The camera 214 includes a detector exposed to a field of view 216 that encompasses at least a portion of the patient 212. In some embodiments, the field of view 216 also encompasses a contact sensor 230 of the patient. In this embodiment, the contact sensor 230 is a pulse oximeter. The pulse oximeter may be similar or identical to the pulse oximeters described above with respect to FIGS. 1A and/or 1B. In various embodiments, the contact sensor 230 may be different or additional types of sensors that can emit signals that are received/captured by the non-contact detector 210 as disclosed herein. In some embodiments, signals may also be sent from the detector (e.g., camera) to the sensor (e.g., oximeter) as disclosed herein.

The camera 214 generates a sequence of images over time. A measure of the amount, color, and/or brightness of light within all or a portion of the image over time is referred to as a light intensity signal. In some embodiments, each image includes a two-dimensional array or grid of pixels, and each pixel includes three color components—for example, red, green, and blue. A measure of one or more color components of one or more pixels over time is referred to as a pixel signal, which is a type of light intensity signal. The camera operates at a frame rate, which is the number of image frames taken per second (or other time period). Example frame rates include 20, 30, 40, 50, or 60 frames per second, greater than 60 frames per second, or other values between those. Frame rates of 20-30 frames per second produce useful signals, though frame rates above 50 or 60 frames per second are helpful in avoiding aliasing with light flicker (for artificial lights having frequencies around 50 or 60 Hz).

The detected images are sent to a monitor 224, which may be integrated with the camera 214 or separate from it and coupled via wired or wireless communication with the camera (such as wireless communication 220 shown in FIG. 2A). The monitor 224 includes a processor 218, a display 222, and hardware memory 226 for storing software and computer instructions. Sequential image frames of the patient are recorded by the video camera 214 and sent to the processor 218 for analysis. The display 222 may be remote from the monitor 224, such as a video screen positioned separately from the processor and memory. Other embodiments of the monitor 224 may have different, fewer, or additional components than the monitor 224 shown in FIG. 2A.

The detected images can be processed or analyzed to determine a signal being emitted from the contact sensor 230, such as a light signal. Different methods for identifying the signal are contemplated. For example, a light used by a pulse oximeter to measure pulse is typically red in color. Accordingly, the detected images may be analyzed to find red light and thereby identify the light signal for further decoding and processing. In another example, the system may recognize aspects of the light signal over time from subsequent detected images, such as a frequency, phase, or amplitude of the signal, or a pattern encoded in the signal. In another example, the system may identify objects in the detected images, such as a patient, a specific part of the patient (e.g., hand, mouth, face, torso, etc.), a contact sensor or associated monitor device, bed, or any other object in the detected images. The system may then use the locations of such identified objects to deduce an approximate or expected location of a light signal to be detected. For example, if the system detects a human hand, it may focus processing power on the area of and around the hand to look for a light signal being emitted from a pulse oximeter worn on a patient's finger as in FIG. 2A. As described herein, the video camera 214 can also be instructed to adjust its field of view 216, focus, or zoom based on a detection of something in an image. In this way, the system may be able to focus on an identified area (such as a human hand) to better analyze that area for a light signal. An intensity of an emitted light signal may also be detected by the system in order to identify the light signal. In some embodiments, more than one method may be used in combination to better detect and identify an emitted light signal, including any of the methods described herein. In some embodiments, additional methods of identifying a signal from detected images may also be used.

Figure 2B:
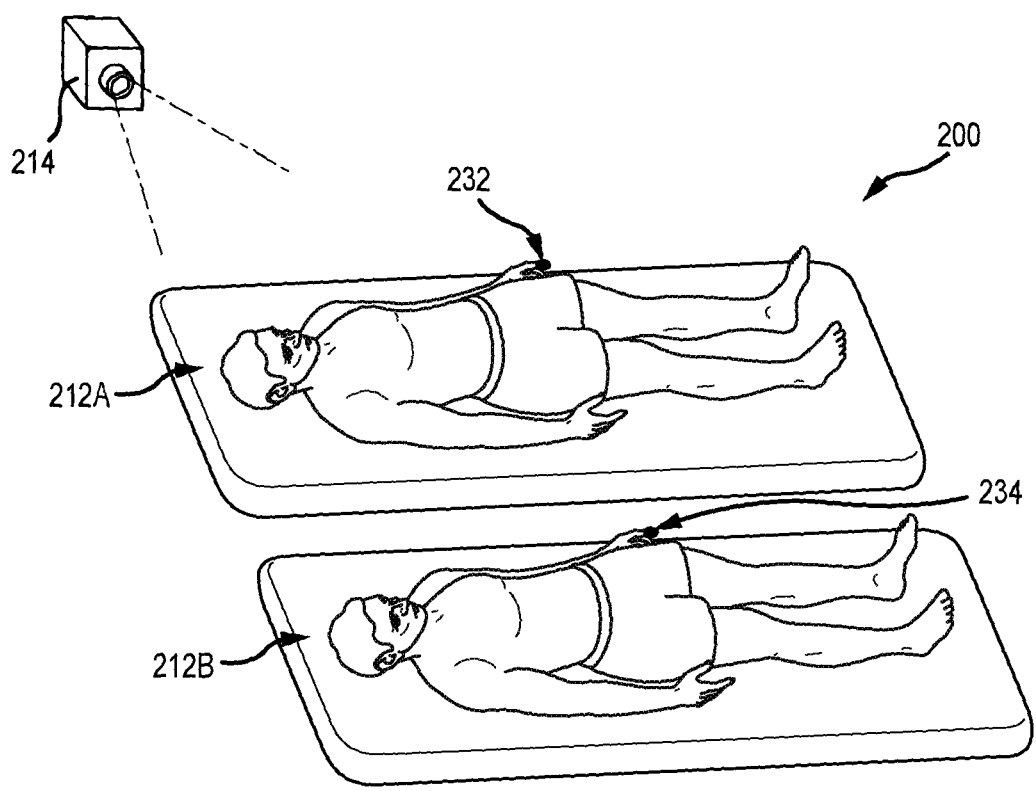
FIG. 2B is a schematic view of a video-based patient monitoring system monitoring multiple patients according to various embodiments described herein.

FIG. 2B is a schematic view of a video-based patient monitoring system 200 monitoring multiple patients, such as patients 212A and 212B, according to an embodiment of the invention. Because the detector 214 in the system is non-contact, it can be used to monitor more than one patient, contact sensor, and/or other device at the same time. A method for monitoring two or more patients, contact sensors, and/or other devices at the same time includes orienting the field of view of the camera 214 to encompass two or more patients, such as the patients 212A and 212B. In an embodiment, the camera 214 is oriented such that the field of view encompasses a contact sensor 232 and 234 of each of the patients 212A and 212B, respectively. A single camera system can then be used to receive signals from the contact sensors 232 and 234 to measure vital signs from multiple patients, such as patients on a general care floor, or to track movement of patients within a room or ward as disclosed herein. For example, the system may track when a patient enters and/or exits the field of view 216 of the camera 214 to determine where a patient is and when.

The patients can be identified based on signals from the contact sensors 232 or 234, or from other information captured by the camera 214, such as a barcode or other optical information indicating the identity of the patient. Such optical information may be located on the patient, such as on a bracelet, or on a bed or gurney of the patient, or elsewhere near the patient. The system may also identify traits of a patient to identify or increase confidence in a determination of an identity of the patient. For example, the system may match known hair color, body type, skin color, etc. observed in the detected images with known information about a patient. This information can be used in combination with the barcode or other optical identification information detected from the detected image to make sure the system has correctly identified the patient. Other biometric data may also be used to perform this identification or increase confidence in the identification. For example, pulse patterns, vein patterns, finger prints, and any other kind of biometric information may be detected and used to identify a patient. Such information may be collected by the contact sensors and transmitted to the camera with light signals as disclosed herein. For example, a pulse oximeter may also be capable of imaging and/or reading a patient's fingerprint. That fingerprint may be encoded into a light signal and emitted for the video camera to capture. The monitoring system can then decode that information and use the fingerprint image information to identify a patient or verify a patient's identity. In this way, the system can accurately track patients, even if sensors are switched to different patients and/or patients are moved around within or outside a healthcare facility.

Figure 3:
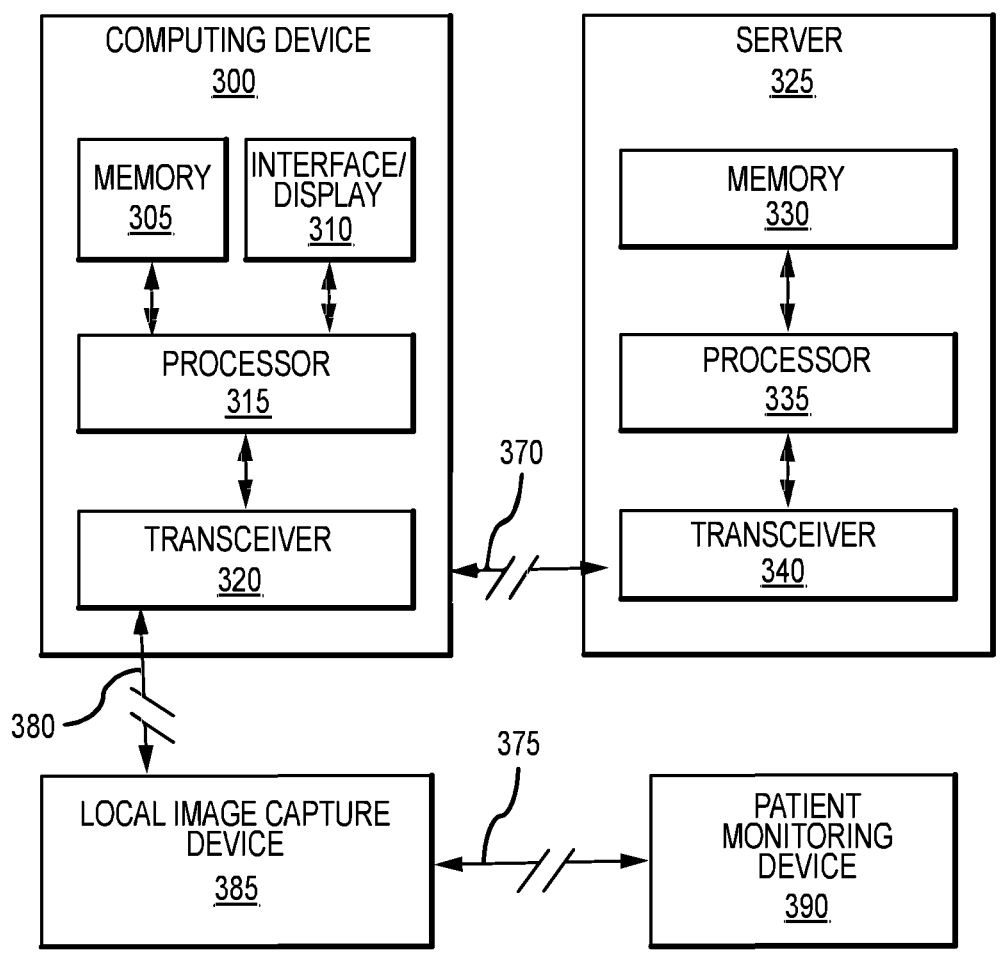
FIG. 3 is a block diagram illustrating a computing device, a server, a local image capture device, and a patient monitoring device according to various embodiments described herein.

FIG. 3 is a block diagram illustrating a computing device 300, a server 325, a local image capture device 385, and a patient monitoring device 390 according to an embodiment of the invention. In various embodiments, fewer, additional and/or different components may be used in a system. The computing device 300 includes a processor 315 that is coupled to a memory 305. The processor 315 can store and recall data and applications in the memory 305, including applications that process information and send commands/signals according to any of the methods disclosed herein. The processor 315 may also display objects, applications, data, etc. on an interface/display 310. The processor 315 may also receive inputs through the interface/display 310. The processor 315 is also coupled to a transceiver 320. With this configuration, the processor 315, and subsequently the first party computing device 300, can communicate with other devices, such as the server 325 through a connection 370 and the local image capture device 385 through a connection 380. For example, the first party computing device 300 may send to the server 325 information determined about a patient from a light signal captured by the local image capture device as disclosed herein. The computing device 300 may be the monitor 224 of FIG. 2A, or it may be a different computing device that the monitor 224 of FIG. 2A communicates with through a hard line or wireless connection. Accordingly, the computing device 300 may be located remotely from the local image capture device 385 and the patient monitoring device 390, or it may be located close to those devices (e.g., in the same room). In some embodiments where the computing device 300 and the monitor 224 are separate devices, the local image capture device 385 may include the monitor 224 of FIG. 2A.

In some embodiments, the local image capture device 385 is a video camera, such as the camera 214 of FIGS. 2A and 2B. The image capture device 385 is described as local because it is close in proximity to the patient monitoring device 390. That is, the patient monitoring device 390 is (at least at some time) within the field of view of the local image capture device 385. The video camera captures light signals from the patient monitoring device 390 as disclosed herein. The patient monitoring device 390 may be, for example, a pulse oximeter. In this way, light signals emitted by the patient monitoring device 390 may be captured through a connection 375 by the local image capture device 385 and transmitted to the computing device 300 through the connection 380. In some embodiments, the computing device 300 may also send a message to the local image capture device 385 through the connection 380, and that message or an associated message may be transmitted to the patient monitoring device 390 as disclosed herein.

The server 325 includes a processor 335 that is coupled to a memory 330. The processor 335 can store and recall data and applications in the memory 330. The processor 335 is also coupled to a transceiver 340. With this configuration, the processor 335, and subsequently the server 325, can communicate with other devices, such as the computing device 300 through the connection 370.

The devices shown in the illustrative embodiment may be utilized in various ways. For example, any of the connections 370, 375, and 380 may be varied. Any of the connections 370, 375, and 380 may be a hard-wired connection. A hard-wired connection may involve connecting the devices through a USB (universal serial bus) port, serial port, parallel port, or other type of wired connection that can facilitate the transfer of data and information between a processor of a device and a second processor of a second device. In another embodiment, any of the connections 370, 375, and 380 may be a dock where one device may plug into another device. While plugged into a dock, the client-device may also have its batteries charged or otherwise be serviced. In other embodiments, any of the connections 370, 375, and 380 may be a wireless connection. These connections may take the form of any sort of wireless connection, including, but not limited to, Bluetooth connectivity, Wi-Fi connectivity, infrared, visible light, radio frequency (RF) signals, or other wireless protocols/methods. For example, other possible modes of wireless communication may include near-field communications, such as passive radio-frequency identification (RFID) and active RFID technologies. RFID and similar near-field communications may allow the various devices to communicate in short range when they are placed proximate to one another. In an embodiment using near field communication, two devices may have to physically (or very nearly) come into contact, and one or both of the devices may sense various data such as acceleration, position, orientation, velocity, change in velocity, IP address, and other sensor data. The system can then use the various sensor data to confirm a transmission of data over the internet between the two devices. Other RFID systems include an RFID tag (e.g., at a contact sensor) that responds to a signal from an RFID reader (e.g., at a local capture device). In this example, the local capture device is not an image capture device. In such an embodiment, the RFID reader sends a signal that causes the RFID tag to transmit pre-stored or requested data. In some embodiments, the signal from the RFID reader can power the circuitry of the RFID tag to transmit the requested information and/or acquire the requested information (e.g., through measuring a vital sign). In some embodiments, signals from the reader may also be used to charge a battery or capacitor at the contact sensor. In yet another embodiment, the various devices may connect through an internet (or other network) connection. That is, any of the connections 370, 375, and 380 may represent several different computing devices and network components that allow the various devices to communicate through the internet, either through a hard-wired or wireless connection. Any of the connections 370, 375, and 380 may also be a combination of several modes of connection.

To operate different embodiments of the system or programs disclosed herein, the various devices may communicate in different ways. For example, the computing device 300 may download various software applications from the server 325 through the internet. Such software applications may allow the various devices in FIG. 3 to perform some or all of the processes, functions, and methods described herein. In another embodiment, the computing device 300 may operate using internet browsers that can access websites that perform the functionality of any of the processes, functions, and methods disclosed herein. Additionally, the embodiments disclosed herein are not limited to being performed only on the disclosed devices in FIG. 3. It will be appreciated that many various combinations of computing devices may execute the methods and systems disclosed herein. Examples of such computing devices may include other types of medical sensors, contact sensors, non-contact sensors, vital sign sensors, infrared cameras/detectors, night vision cameras/detectors, other types of cameras, radio frequency transmitters/receivers, smart phones, personal computers, servers, laptop computers, tablets, blackberries, RFID enabled devices, or any combinations of such devices.

The configuration of the devices in FIG. 3 is merely one physical system on which the disclosed embodiments may be executed. Other configurations of the devices shown may exist to practice the disclosed embodiments. Further, configurations of additional or fewer devices than the ones shown in FIG. 3 may exist to practice the disclosed embodiments. Additionally, the devices shown in FIG. 3 may be combined to allow for fewer devices than shown or separated such that more than the four devices exist in a system.

Figure 4:
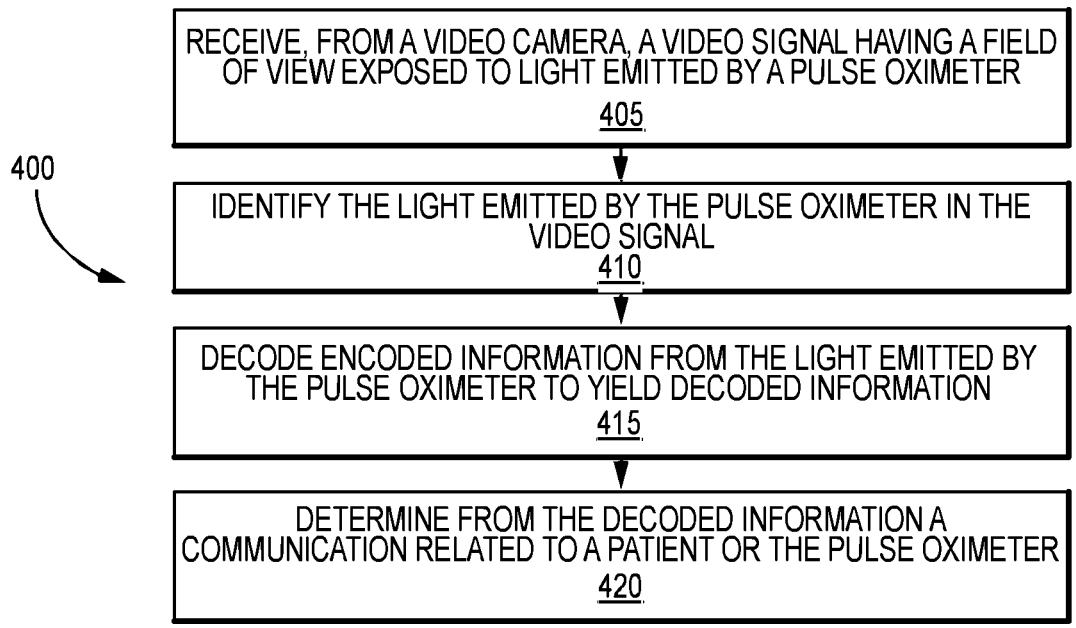
FIG. 4 is a flowchart of a method for receiving information from a pulse oximeter through a video camera according to various embodiments described herein.

FIG. 4 is a flowchart of a method 400 for receiving information from a pulse oximeter through a video camera according to an embodiment of the invention. The method includes receiving, from a video camera, a video signal having a field of view exposed to light emitted by a pulse oximeter at 405. The light includes encoded information. For example, the light may include information related to a measurement taken by the pulse oximeter, the patient being measured, or the pulse oximeter itself. The pulse oximeter is an example of the contact sensors described herein, such as those shown in FIGS. 1A, 1B, 2A, 2B, and 3 as described above.

The method 400 further includes identifying, using a processor, the light emitted by the pulse oximeter in the video signal at 410. This may be done through video/image processing to identify the light signal being emitted. As disclosed herein, the light may be identified based on a color, frequency, amplitude, phase, location, and/or intensity of the light. A proximity of the light source to another identifiable object in the image, or any other method for identifying the light signal in the video signal images, may be used. The processor may be the processor of, for example, the monitor 224 of FIG. 2B and/or the processor of the computing device 300 of FIG. 3.

The method 400 further includes decoding, using the processor, the encoded information of the light emitted by the pulse oximeter at 415. Decoding the encoded information yields decoded information. Many signals include information that is encoded. For example, frequency modulation schemes are often used to encode information into a signal to make the information less likely to be corrupted by noise or inefficiencies in accurately transmitting and/or receiving signals. Other modulation, encoding, or transmission schemes may also be used, such as a pulse width or amplitude modulation.

The method 400 further includes determining, using the processor, from the decoded information a communication related to a patient or the pulse oximeter at 420. For example, the communication may be a first communication related to a patient such as the patient's pulse, other vital sign measurement of the patient, or a unique identifier associated with the patient. The communication may also be a second communication associated with the pulse oximeter, such as a configuration of the pulse oximeter, an alert condition of the pulse oximeter, other state/status of the pulse oximeter, or a unique identifier associated with the pulse oximeter. As disclosed herein, the light signal emitted by the pulse oximeter may also be used by the pulse oximeter to measure a vital sign of the patient, or the light signal may be a separate light source from the one used to measure a vital sign of the patient. In such an example, the light emitted by the pulse oximeter is a dedicated light for the purpose of sending the encoded information. Such a dedicated light may be located at an outer portion of a probe of the pulse oximeter, at a cable of the pulse oximeter, or at a base of the pulse oximeter. The probe may be the sensor 112 as shown above in FIGS. 1A and 1B. The base of the pulse oximeter may be the monitor 110 as shown above in FIGS. 1A and 1B.

Various embodiments may have different, additional, or fewer steps or components. For example, the signals emitted may not be light signals, but may instead be radio frequency signals. In other examples, the light may not be visible light. For example, infrared light may be used. In other examples, sensors other than a pulse oximeter may be used, such as a temperature sensor.

Figure 5:
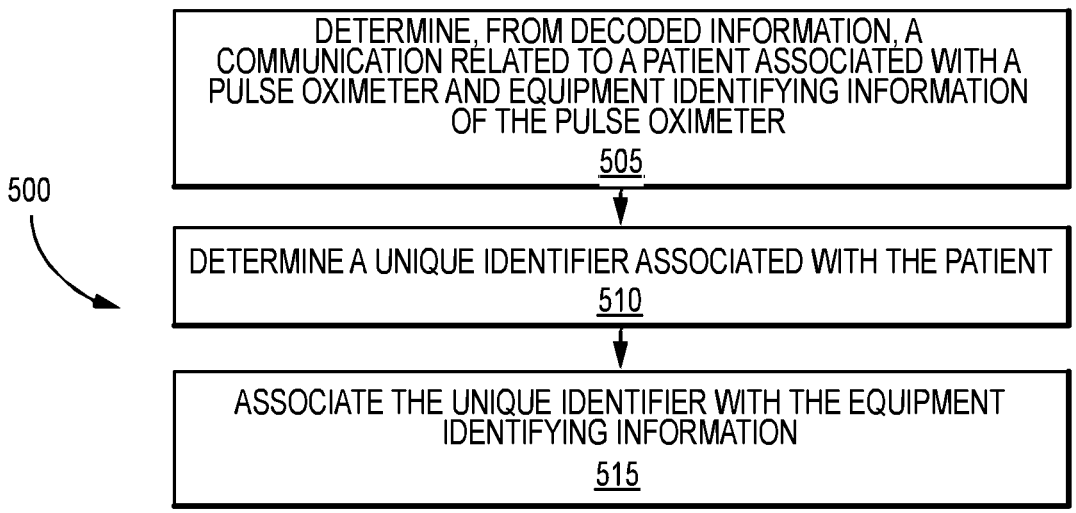
FIG. 5 is a flowchart of a method for determining identifying information about a pulse oximeter according to various embodiments described herein.

FIG. 5 is a flowchart of a method 500 for determining identifying information about a pulse oximeter according to an embodiment of the invention. The method 500 includes determining, from decoded information, a communication related to a patient associated with a pulse oximeter and equipment identifying information of the pulse oximeter. For example, the communication may include information about the patient wearing the pulse oximeter, and a unique identifier of the pulse oximeter itself. The information about the patient may include information input into the monitor of the pulse oximeter such as a name, identification number, or other information about a patient. The information about the patient could also include a vital sign measurement or biometric information about the patient. The information about the patient may also be information identified from the video signal, such as body type, hair/skin/eye color, height, estimated weight, face shape, or other physical characteristics.

The method 500 further includes using this information about the patient to determine a unique identifier associated with the patient at 510. For example, using FIG. 3 as reference, the computing device 300 may use the information about the patient to compare to data stored in the server 325. For example, the server may store biometric data that is associated with information about a patient's identity and a unique identifier of the patient. By matching the information about the patient (e.g., name, biometric data, vital sign measurement, etc.) to the information on the server, the computing device can determine the unique identifier associated with the patient that is wearing the pulse oximeter.

The method 500 further includes associating the unique identifier of the patient with the equipment identifying information at 515. In this way, the patient wearing the pulse oximeter is associated with that pulse oximeter and any information known about the pulse oximeter. For example, the pulse oximeter may be assigned to a particular room in a hospital. By associating the patient with the pulse oximeter, the system can identify or verify what room the patient is in. The information known about the pulse oximeter may be manually input by a healthcare professional or may be determined by the system. For example, the pulse oximeter may have location sensing capabilities using various technologies such as Bluetooth, Wi-Fi, GPS, etc. If a pulse oximeter can be relocated, the data can be manually or automatically updated. If a pulse oximeter is installed as a permanent fixture in a hospital room, the location information can be determined once and then not changed. The information (e.g., location information) about sensors such as pulse oximeters may also be stored in the server 325. Other sensor information may include information about how a sensor is calibrated or a sensor's default capabilities. By having this information, the system can contextualize certain information about the sensor and the patient. For example, if a sensor is made for a small child, but the patient identified is a large adult, the system may identify an alert condition that the sensor cannot adequately be used to monitor a vital sign of the patient.

Figure 6:
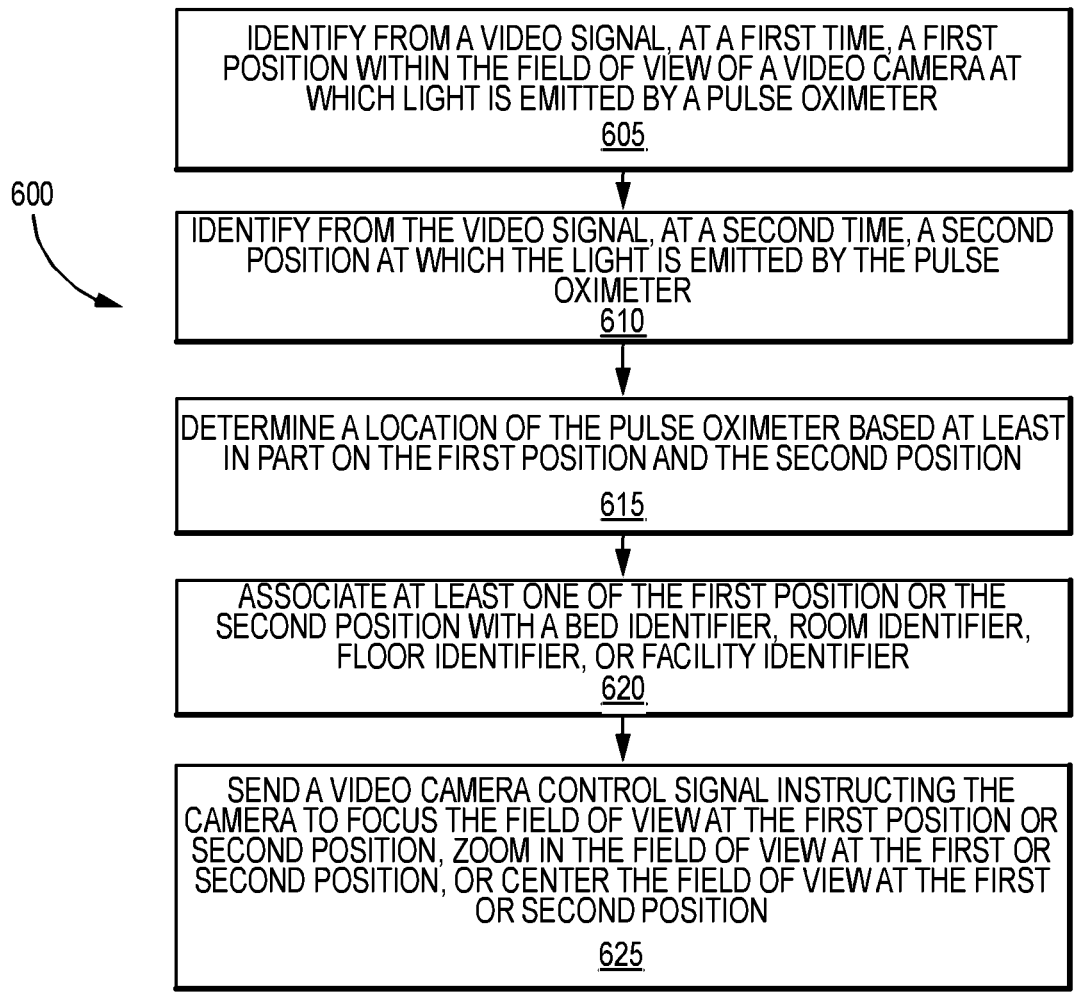
FIG. 6 is a flowchart of a method for determining a location of a pulse oximeter within a field of view of a camera according to various embodiments described herein.

FIG. 6 is a flowchart of a method 600 for determining a location of a pulse oximeter within a field of view of a camera according to an embodiment of the invention. The method 600 includes identifying from the video signal, at a first time, a first position within the field of view of the video camera at which the light is emitted by the pulse oximeter at 605. Each image captured by a video camera includes a two-dimensional array or grid of pixels. Once the light signal is identified, the system can determine or identify a first position of that light signal in the two-dimensional array or grid of pixels. In some embodiments, the system may further identify a third coordinate for three-dimensional location of a light signal in an image. For example, a proximity sensor may be used in combination with the video signal to determine how far away the source of the light signal is from the camera.

The method 600 further includes identifying from the video signal, at a second time, a second position at which the light is emitted by the pulse oximeter at 610. If the patient has moved, the second position should be different from the first position. If the patient has not moved, the first and second positions should be the same. If the camera moves, changes focus, zooms, or otherwise adjusts, the system should take those adjustments into account to determine if the change in position between the first and second times actually corresponds with a meaningful movement of the patient (or more generally the light source).

The method 600 further includes determining, using the processor, that the first position is different from the second position by a threshold amount. In so doing, the system determines the location of the pulse oximeter based at least in part on the first position and the second position at 615. In some embodiments, if the patient or light source has moved more than a threshold amount, an alarm condition may be identified and triggered by the system. For example, it may be undesirable for a patient with mobility issues to leave their bed and/or hospital room without assistance. In such an embodiment, additional logic can be applied to determine whether an alarm condition should be triggered. For example, if the patient or light source moves the threshold distance, but the system detects another person in the images captured by the video camera, then an alarm condition is not triggered. If the patient or light source moves the threshold distance, but the system does not detect another person, then an alarm condition is triggered.

In some embodiments, the second position may be on an edge of the field of view of the camera. The system may be able to determine if the patient or light source left the field of view of the camera if the patient or light source is not in the images captured by the camera after the second time. In other words, the system determines that, based on the threshold amount, the pulse oximeter has moved beyond the field of view of the video camera or has moved the predetermined threshold distance within the field of view of the video camera. Depending on where the second position is, further information may be determined. For example, if the second position is near a known doorway in an image, and the light source is not found in an image captured after the second time, the system can determine that the light source and patient went through the doorway. This may too have different consequences. For example, if the doorway is to a bathroom, the system may do nothing. If the doorway is to a hallway, the system may trigger an alarm condition that the patient has left their room. In another example, the first position may be at an edge of a field of view and the second position may be further within the field of view of a camera. In such an example, the system may recognize that a new patient has entered the room or field of view and may initiate a process to identify the patient as disclosed herein. The system may also update a database indicating that a patient has left or arrived at a particular location tracked by a particular camera. In this way, the system can associate at least one of the first position or the second position with a bed identifier, room identifier, floor identifier, or facility identifier at 620. In other words, how the patient moves within the field of view of the camera can change how the system updates an identified location of the patient/sensor. In these examples, logic and multiple cameras in multiple locations may be utilized to better determine the locations and/or movements of a patient/sensor. Each time the patient comes into view of a new camera, the methods of FIGS. 4 and/or 5 may be utilized to verify the patient's and/or sensor's identity to accurately track the patient/sensor movements.

In another example, if the patient/light source is one of many in a hospital ward observable by the same camera, the first and second positions may be tracked by the system to ensure that a patient does not interfere with other patients in the ward. Such a system can protect patients from one another, both physically and/or to prevent the spread of infectious diseases. In some embodiments, the system may perform this tracking by identifying the patient in the video signal instead of the light source/sensor. The system may also track how long a patient is out of view of the camera. For example, if the patient is in the bathroom for longer than a threshold time (e.g., 30 minutes), an alert condition may be triggered so that the patient can be checked on.

The system may also use the first and second positions collected at the first and second times to track trajectory and velocity of a patient or sensor. For example, such tracking may identify if a patient has fallen: rapid change in position along with a downward change in absolute position on the grid of pixels may indicate a fall, for example. Such information may trigger an alert condition and allow a patient to be helped faster.

The method 600 further includes sending a video camera control signal instructing the camera to change its field of view in some way at 625. This may be based on a movement of the patient as identified in 605, 610, 615, and/or 620. The video camera control signal instructs the camera to focus the field of view at, zoom in the field of view, or center the field of view. This adjustment of the camera may be for a variety of reasons. For example, the camera may adjust to keep a patient/sensor near the center of the camera's field of view. Accordingly, the determined second position of the patient/sensor may be used to adjust the camera. The camera may also adjust to better read the light signal being emitted from the sensor. By tracking the location of the light signal as disclosed herein, the camera can identify where to zoom in, move, or focus to get a better picture of the signal. In this way, the system has a higher likelihood of receiving the signal in a manner that allows the system to decode the signal and understand the information in the signal. The camera may also be adjusted for privacy reasons, or periodically adjusted to scan a room for additional patients, sensors, or other items of interest. In some embodiments, the camera may be instructed to adjust its field of view based on an identified alarm condition. For example, if a patient has a dangerous pulse level, the camera may be instructed to identify that patient in the field of view and zoom in, center on, and/or focus on that patient. This video feed can then be patched to a remote monitoring facility to help healthcare providers determine how to best take remedial action.

Figure 7:
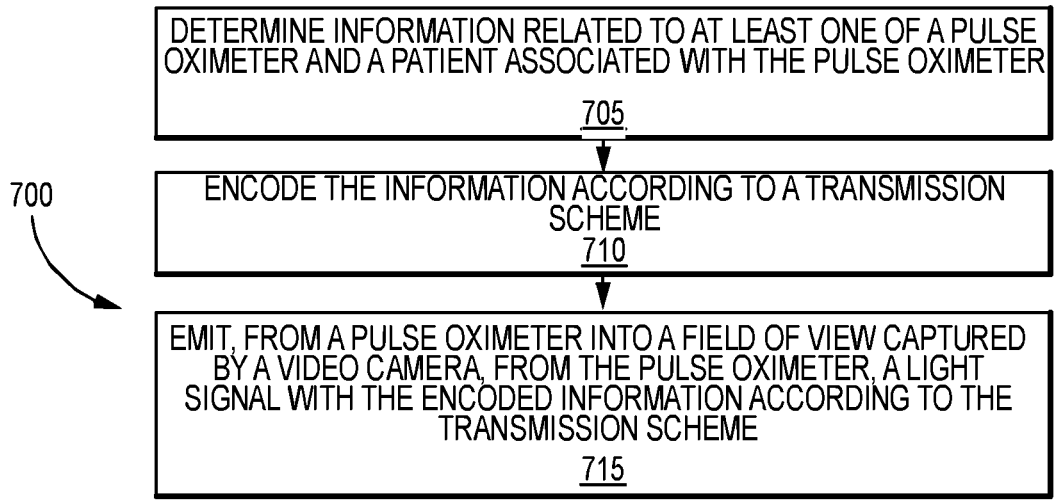
FIG. 7 is a flowchart of a method for sending information from a pulse oximeter according to various embodiments described herein.

FIG. 7 is a flowchart of a method 700 for sending information from a pulse oximeter according to an embodiment of the invention. The method 700 communicates information from a patient monitoring device and includes determining information related to at least one of a pulse oximeter and a patient associated with the pulse oximeter at 705. The method further includes encoding the information according to a transmission scheme at 710. The method further includes emitting, from the pulse oximeter, a light signal with the encoded information according to the transmission scheme at 715. The light signal is emitted in a field of view captured by a video camera. The method 700 describes steps for sending a message from the perspective of the patient monitoring device. The message may be prompted by a request message from a camera or other system. The message may also be routinely or periodically transmitted by the patient monitoring device. The message may also include any of the information described herein that may be transmitted from the patient monitoring device to a non-contact monitoring system, such as vital sign information, biometric information, information about the patient monitoring device, location information, etc.

Figure 8:
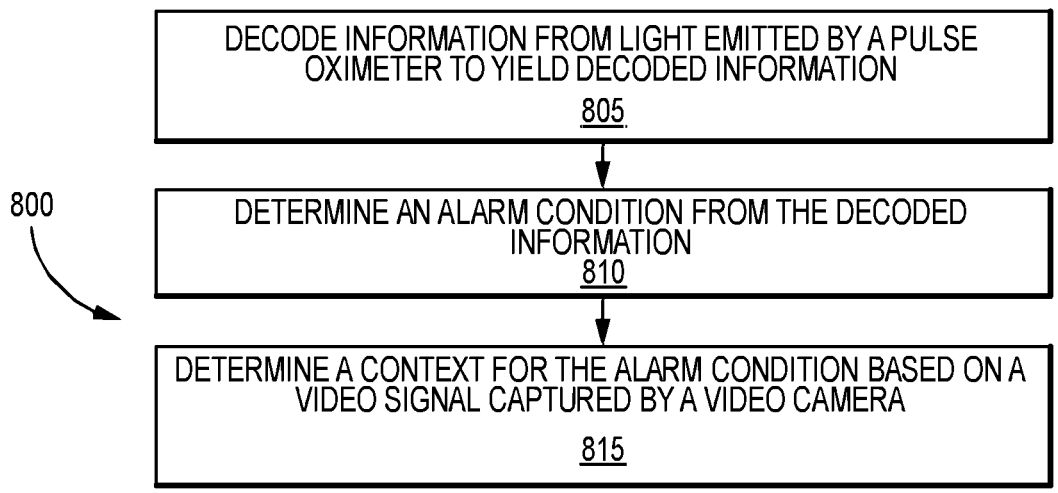
FIG. 8 is a flowchart of a method for determining an alarm condition based on information sent from a pulse oximeter according to various embodiments described herein.
Figure 10:
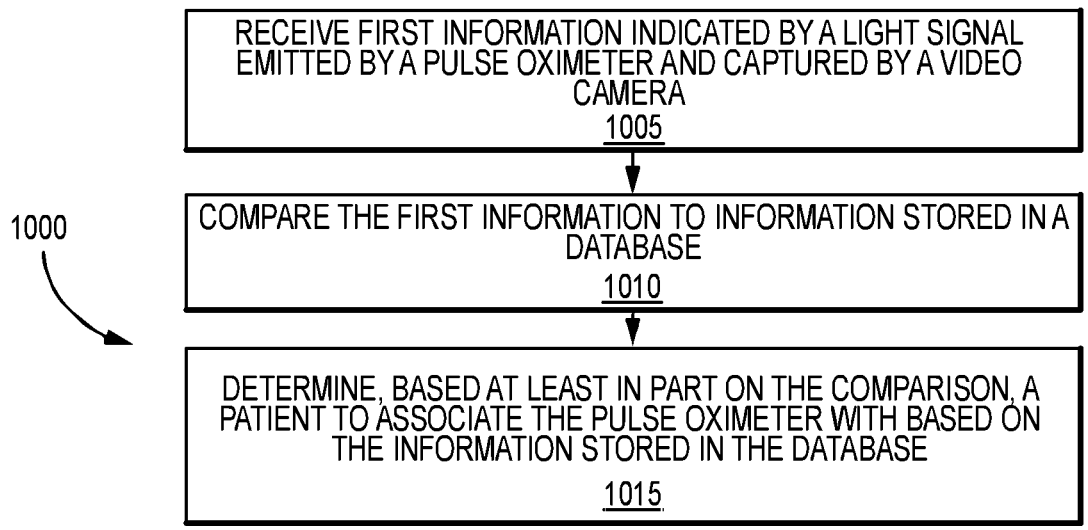
FIG. 10 is a flowchart of a method for verifying information from a pulse oximeter according to various embodiments described herein.

FIG. 8 is a flowchart of a method 800 for determining an alarm condition based on information sent from a pulse oximeter according to an embodiment of the invention. The method includes decoding information from light emitted by a pulse oximeter to yield decoded information at 805. The method further includes determining an alarm condition from the decoded information at 810. The method further includes determining a context for the alarm condition based on a video signal captured by a video camera at 815. As described herein, various alarm conditions can be detected by the system. For example, if a pulse oximeter is not detecting a pulse or is detecting an irregular pulse, an alarm may be generated that a patient is not well. Such instances can be contextualized using information from a video signal. For example, processing of the video signal can indicate if the pulse oximeter has fallen off, or if the patient removed it to use the restroom. Such contexts may not necessitate an alarm condition. In some embodiments, the alarm condition may be communicated as part of the information in the light signal sent from the patient monitoring device to the camera. In other embodiments, an alarm condition may be initiated when information about a patient, patient location, or sensor information does not match what the system is expecting. In other words, an alarm may be initiated when patient identification information known or sensed by the system does not match what is stored in a database. For example, a healthcare professional inputs into a database that patient A will be put in room 101 at a hospital. The non-contact monitoring system will use a light signal from a sensor in room 101 to determine the identity of the patient in room 101. If the system determines that the patient in room 101 is patient B, that determination would not match the expected information entered into the database. Accordingly, the system may update the database to reflect the actual observed condition or may initiate an alarm condition so that attention can be given by healthcare provider staff to resolve the issue. In other words, the systems and methods disclosed herein provide for redundancies and quality assurance checks to reduce errors, mishandling of patients, and other mishaps that can reduce quality of care and increase costs of care and inefficient use of resources. Where identified errors may not be prevented, the system can also allow for them to be expeditiously corrected before larger errors take place or the effects of the error are compounded. FIG. 10 and its accompanying description below provide additional embodiments of how the database is used to improve existing systems and methods.

In some embodiments, the systems and methods disclosed herein may also be used to suppress alarm conditions. For example, an alarm may be triggered by a sensor or other condition as disclosed herein. Information from the images or video feed captured by a camera can be used to suppress the alarm condition (i.e., shut off or disable the alarm). In some cases, the information from the images or video feed may also yield a different type of alarm condition to be initiated, even though a first alarm condition is suppressed.

In an embodiment, a pulse oximeter may be the sensor used, and an alarm condition may be triggered based on an irregular pulse measurement from the pulse oximeter. The system may receive the indication of the alarm condition, and in response analyze the video feed from a camera where that pulse oximeter is known to be within the field of view (e.g., through previously identifying the pulse oximeter using methods as disclosed herein). In the video feed, the system may recognize a condition that indicates the alarm should be suppressed. For example, if the pulse oximeter has fallen off the patient's finger, the pulse oximeter has started slipping off or is otherwise misplaced on the patient so that an accurate reading cannot be made, or the patient is moving too erratically to make an accurate measurement, the system may determine that the original alarm condition for an irregular pulse measurement should be suppressed. Additionally, the system may generate a different alarm condition that a health care professional should check on the patient to make sure the pulse oximeter is properly placed on the patient or otherwise check on the patient. In some embodiments, the second alarm condition may be more or less urgent than the first alarm condition. For example, if the system determines that the patient's pulse oximeter has fallen off, the alarm to replace the pulse oximeter may have a lower urgency level than the irregular pulse alarm. This can lead to more efficient use of resources, as health care staff would not need to attend to a misplaced pulse oximeter as quickly as they would someone who had an irregular pulse. Conversely, if the video analysis yields that an accurate measurement cannot be taken from the pulse oximeter because the patient is moving too erratically, the system may initiate a more urgent alarm condition. In this case, the video monitoring helps identify a condition that is more dangerous or urgent than just an irregular pulse might be. In this way, the non-contact monitoring systems disclosed herein can help suppress alarms and can help initiate different urgency leveled alarms to help a health care facility more efficiently use resources while providing better care for their patients.

Figure 9:
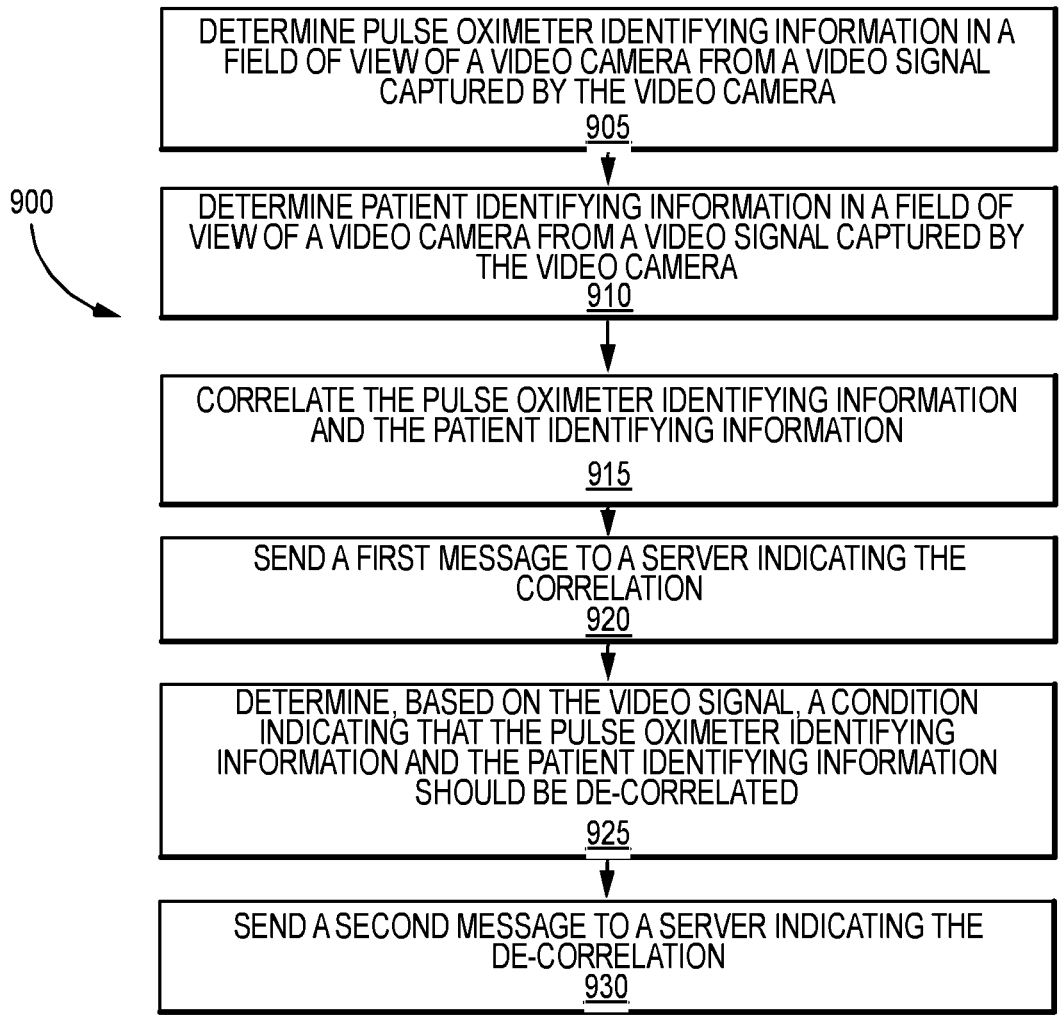
FIG. 9 is a flowchart of a method for associating a pulse oximeter with a patient according to various embodiments described herein.

FIG. 9 is a flowchart of a method 900 for associating a pulse oximeter with a patient according to an embodiment of the invention. The method includes determining pulse oximeter identifying information in a field of view of a video camera from a video signal captured by the video camera at 905. The method further includes determining patient identifying information in a field of view of a video camera from a video signal captured by the video camera at 910. The method further includes correlating the pulse oximeter identifying information and the patient identifying information at 915. In this way, once a patient has been identified, that patient can be associated with the pulse oximeter. The system may then be able to keep track of a patient if the patient moves with the pulse oximeter or other sensor still attached.

The method also includes sending a first message to a server indicating the correlation at 920. In other words, the system is updated according to the new correlation. The method also includes determining, based on the video signal, a condition indicating that the pulse oximeter identifying information and the patient identifying information should be de-correlated at 925. This condition may be based on manually input information that the patient is no longer at the room or healthcare facility. The condition may also be information that the patient has gone a certain threshold amount of time without wearing or otherwise being associated with the sensor. The condition may also be that a different patient is now associated with the sensor. In this instance, a new correlation may also be made, and the system/server can be updated accordingly. The method also includes sending a second message to a server indicating the de-correlation at 930, updating the system/server based on the determined condition.

FIG. 10 is a flowchart of a method 1000 for verifying information from a pulse oximeter according to an embodiment of the invention. The method includes receiving first information indicated by a light signal emitted by a pulse oximeter and captured by a video camera at 1005. The method further includes comparing the first information to information stored in a database at 1010. The method further includes determining, based at least in part on the comparison, a patient to associate the pulse oximeter with based on the information stored in the database at 1015. In other words, the system can take information gathered by the pulse oximeter and/or camera and use the information to identify the patient based on information stored in a database. In an alternative embodiment and as disclosed herein, such information may be information about the patient (e.g., biometric, vital signs, other physical characteristics), or may be some other kind of information. For example, when a patient is checked in, they may have a bracelet, chart, sticker, pin, clothing, or other information given to them that has optically identifiable information on it. For example, it may have their name in text that can be optically recognized, or it may have other optically recognizable features such as a QR code, bar code, color coordinated code, or other type of code that can be identified by the camera. The system can use this identified information to associate the information from the code with a patient in the system. In this way, a patient may be easily and quickly identified by information from the pulse oximeter or by other visual information collected by the camera. In a similar way, a bar code or other optical identifier may also be placed on the sensor/pulse oximeter to allow for easy identification of the sensor device. Identifying the sensor device or device type may also instruct the system of what type of signal to look for. For example, certain pulse oximeters may have lights that blink at different frequencies, so identifying the type of sensor can help the system identify, locate, and understand a light signal emitted by the sensor. In other embodiments, the aspects of the signal itself may be used to identify what type of sensor is being used. For example, a light signal at frequency A may be associated with a first type of sensor, while a light signal at frequency B may be associated with a second type of sensor. In some embodiments, information about a sensor interpreted by the systems and methods disclosed herein may be utilized to determine how to process information from the sensor. For example, if a light signal at frequency A is detected, frequency A may be known by the system to be associated with a first manufacturer type of device. The system may also identify that the first manufacturer does not design its devices to specially communicate with a video-based monitoring system. Accordingly, the system may not monitor such a device or may only monitor certain aspects or signals associated with the device of the first manufacturer. In another example, a frequency B signal may indicate a second manufacturer device that is compatible with more of the features and methods disclosed herein. By properly identifying the frequency or other aspect of a signal from a particular device, the system can therefore better understand what information and what types of information to try to gather and identify from a video feed of an identified device.

Figure 11:
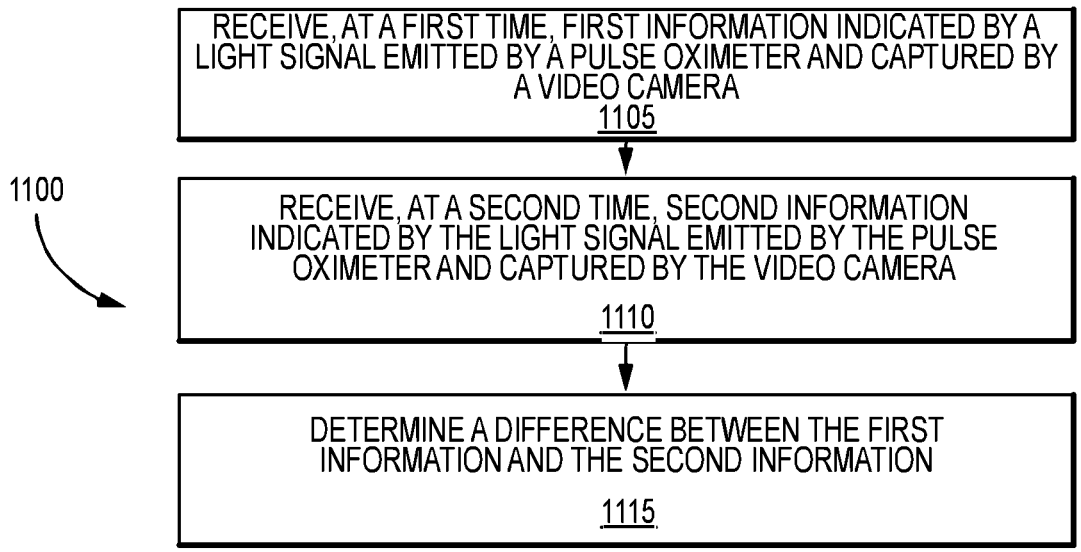
FIG. 11 is a flowchart of a method for tracking information over time from a pulse oximeter according to various embodiments described herein.

FIG. 11 is a flowchart of a method 1100 for tracking information over time from a pulse oximeter according to an embodiment of the invention. The method includes receiving, at a first time, the first information indicated by a light signal emitted by a pulse oximeter and captured by a video camera at 1105. The method further includes receiving, at a second time, second information indicated by the light signal emitted by the pulse oximeter and captured by the video camera at 1110. The method further includes determining a difference between the first and second information at 1115. As one example, a pulse oximeter tracks a patient's pulse. The method 1100 tracks that patient's pulse over time. If there is a change that is determined to be dangerous or otherwise noteworthy, the system may generate an alarm condition based on the change. The changes and differences may also be saved in a system by a database. The system may also use the information for billing purposes. For example, if a certain piece of equipment is used for a certain amount of time, billing for that equipment may be automatically generated based on the tracked time that the equipment was used. In another embodiment, the system may compare in the information indicated to similar information collected in a different way. For example, information received through the light signals may be compared to pulse data collected by the pulse oximeter itself. In this way, redundancies and quality assurance checks can be run to ensure that equipment is functioning the way it is supposed to, and/or that the light signals being received by the camera area being accurately received and decoded. In some embodiments, the system can take a pulse oximetry reading from the red light emitted by the pulse oximeter and detected by the video camera. The oximetry reading detected by the video camera may be read by the video camera actually capturing the light from the pulse oximeter that is passed through a patient's finger. In other words, the light signal captured by the video camera may emanate from a light of a pulse oximeter used to measure pulse or the oxygen in blood without the need for additional lights. This information can be compared to the information collected by the photosensor of the pulse oximeter. Accordingly, the encoded information received by the video camera can be vital sign information. In such embodiments, the system may combine the vital sign (e.g., pulse rate) measured by the video monitoring system with the vital sign (e.g., pulse rate) measured by the contact sensor (e.g., pulse oximeter) to create a more robust measurement. This more robust measurement may be calculated using techniques that use multiple measurements/data points to yield to yield a single measurement/data point, such as averaging, weighted averaging, or using a logic to select whichever of the two measurements is more likely to be reliable. In the last example, where the measurement that is more likely to be reliable is selected, the system may use information captured by the video camera to determine which signal is more likely to be reliable, or the system may default to one measurement type over the other.

The light signal may be initially identified from the video images in a variety of ways as described herein. As just one example, the sequence, frequency of modulation or durations of the red-infrared duty cycles at the pulse oximeter probe may be changed over time. This may be detected by the camera system and decoded to provide positive identification of a probe in an image. This alteration of the duty cycle may be instructed by the camera so that at a specific point in time the camera can match a change in cycle at a specific probe with its sent instructions. Where separate LEDs are used from the red pulse oximeter light, the LED may be a color other than that used to measure pulse. In this way, the different color will not be confused with the pulse oximeter light used by a sensor (i.e., use a different spectrum of light). The separate LED may also use different frequencies or other different signal characteristics than the pulse oximeter light. The separate LED may also be flashed during the off period of a duty cycle of the pulse oximeter probe light so as not to interfere with the pulse oximeter measurements.

The systems and methods described here may be provided in the form of tangible and non-transitory machine-readable medium or media (such as a hard disk drive, hardware memory, etc.) having instructions recorded thereon for execution by a processor or computer. The set of instructions may include various commands that instruct the computer or processor to perform specific operations such as the methods and processes of the various embodiments described here. The set of instructions may be in the form of a software program or application. The computer storage media may include volatile and non-volatile media, and removable and non-removable media, for storage of information such as computer-readable instructions, data structures, program modules or other data. The computer storage media may include, but are not limited to, RAM, ROM, EPROM, EEPROM, flash memory or other solid-state memory technology, CD-ROM, DVD, or other optical storage, magnetic disk storage, or any other hardware medium which may be used to store desired information and that may be accessed by components of the system. Components of the system may communicate with each other via wired or wireless communication. The components may be separate from each other, or various combinations of components may be integrated together into a medical monitor or processor or contained within a workstation with standard computer hardware (for example, processors, circuitry, logic circuits, memory, and the like). The system may include processing devices such as microprocessors, microcontrollers, integrated circuits, control units, storage media, and other hardware.

Although the present invention has been described and illustrated in respect to exemplary embodiments, it is to be understood that it is not to be so limited, since changes and modifications may be made therein which are within the full intended scope of this invention as hereinafter claimed.

What is claimed is:

1. A patient monitoring device, comprising:
a wearable sensor comprising at least one light; and
a processor communicatively coupled with the wearable sensor, the processor configured to:
encode information according to a transmission scheme; and
instruct the at least one light of the wearable sensor to emit a light signal with the encoded information according to the transmission scheme, wherein the light signal is emitted in a field of view captured by a video camera,
wherein the at least one light includes a first light that is configured for use in obtaining information regarding a patient and for emitting the light signal with the encoded information according to the transmission scheme.

2. The patient monitoring device of claim 1, wherein the wearable sensor includes an opening through which light emitted by the first light can be seen by a video camera.

3. The patient monitoring device of claim 1, wherein the encoded information relates to at least one of the patient monitoring device and the patient associated with the patient monitoring device.

4. The patient monitoring device of claim 1, wherein the encoded information relates to one or more patient vital signs.

5. The patient monitoring device of claim 1, wherein the encoded information relates to patient monitoring device identifying information.

6. The patient monitoring device of claim 1, wherein the information obtained is patient fingerprint information.

7. The patient monitoring device of claim 1, wherein the light signal is visible light or infrared light.

8. The patient monitoring device of claim 1, wherein the patient monitoring device is a pulse oximeter.

9. The patient monitoring device of claim 1, wherein the encoded information is encoded using frequency modulation.

10. The patient monitoring device of claim 1, wherein the encoded information is encoded using pulse width modulation.

11. The patient monitoring device of claim 1, wherein the encoded information is encoded using amplitude modulation.

12. A patient monitoring device, comprising:
a wearable sensor comprising at least one light; and
a processor communicatively coupled with the wearable sensor, the processor configured to:
encode information according to a transmission scheme; and
instruct the at least one light of the wearable sensor to emit a light signal with the encoded information according to the transmission scheme, wherein the light signal is emitted in a field of view captured by a video camera,
wherein the wearable sensor further comprises an optical sensor configured for receiving external signals, and
wherein the processor is further configured to process external signals and instruct the patient monitoring device based on the processed external signals.

13. The patient monitoring device of claim 12, wherein the external signal is a request for a specific type of information, and the instruction from the processor to the patient monitoring device is to encode the requested information and emit a light signal with the encoded information according to the transmission scheme.

14. A patient monitoring device, comprising:
a wearable pulse oximetry sensor comprising a light emitter and a photodetector for obtaining vital sign information about a patient; and
a processor communicatively coupled with the wearable pulse oximetry sensor, the processor configured to:
encode the vital sign information according to a transmission scheme; and
instruct the light emitter to emit an encoded light signal with the encoded information according to the transmission scheme, wherein the encoded light signal is emitted in a field of view captured by a video camera.

15. The device of claim 14, wherein the vital sign information comprises respiration rate.

16. The device of claim 14, wherein the vital sign information comprises oxygen saturation.

17. The device of claim 14, wherein the vital sign information comprises pulse rate.

18. The device of claim 14, wherein the encoded information further includes an alarm condition.

19. The device of claim 14, wherein the wearable pulse oximetry sensor is a wireless contact sensor.

* * * * *